(12) United States Patent
Li et al.

(10) Patent No.: US 10,385,034 B2
(45) Date of Patent: Aug. 20, 2019

(54) FLAVONOID IL-17A INHIBITORS

(71) Applicant: THE CLEVELAND CLINIC FOUNDATION, Cleveland, OH (US)

(72) Inventors: Xiaoxia Li, Solon, OH (US); Caini Liu, Solon, OH (US); Jun Qin, Solon, OH (US); Liang Zhu, Cleveland Heights, OH (US); Koichi Fukuda, Cleveland Hts., OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 0 days.

(21) Appl. No.: 14/847,307

(22) Filed: Sep. 8, 2015

(65) Prior Publication Data
US 2016/0068502 A1    Mar. 10, 2016

Related U.S. Application Data

(60) Provisional application No. 62/046,243, filed on Sep. 5, 2014.

(51) Int. Cl.
| | | |
|---|---|---|
| *C07D 215/20* | (2006.01) | |
| *C07D 311/60* | (2006.01) | |
| *C07D 311/62* | (2006.01) | |
| *A61K 31/352* | (2006.01) | |
| *C07D 405/04* | (2006.01) | |
| *C07D 498/04* | (2006.01) | |

(52) U.S. Cl.
CPC ......... *C07D 311/62* (2013.01); *A61K 31/352* (2013.01); *C07D 215/20* (2013.01); *C07D 311/60* (2013.01); *C07D 405/04* (2013.01); *C07D 498/04* (2013.01)

(58) Field of Classification Search
None
See application file for complete search history.

(56) References Cited

U.S. PATENT DOCUMENTS

| 2,749,347 A | 6/1956 | Kreysa | |
|---|---|---|---|
| 2006/0276393 A1* | 12/2006 | Milburn | A61K 31/05 514/183 |
| 2008/0234362 A1* | 9/2008 | Chandler | A61K 31/202 514/456 |
| 2011/0275643 A1 | 11/2011 | Liou et al. | |
| 2011/0300154 A1* | 12/2011 | Umetsu | A61K 38/1793 424/158.1 |

FOREIGN PATENT DOCUMENTS

| DE | 547082 | 3/1932 |
|---|---|---|
| EP | 0952135 A1 | 10/1999 |
| GB | 1589294 | 5/1981 |
| WO | 03051805 A2 | 6/2003 |
| WO | 2006024545 A1 | 3/2006 |
| WO | 2013048145 A2 | 4/2013 |
| WO | WO 2013/048145 * | 4/2013 ........... A61K 31/045 |

OTHER PUBLICATIONS

Zhang et al., British Journal of Nutrition, vol. 111, No. 9, pp. 1549-1563.*
Al-Ramli, et al., T H 17-associated cytokines (IL-17A and IL-17F) in severe asthma. Journal of Allergy and Clinical Immunology 123.5 (2009): 1185-1187.
Baumgarten et al., "Synthesis of 3-Amino-and 3-Nitro-2-arylquinolines1." Journal of the American Chemical Society 79.6 (1957): 1502-1505.
Bradley et al., "Synthesis of pyrylium salts of anthocyanidin type. XIX. Synthesis of delphinidin chloride not involving a demethylation process and synthesis of hirsutidin chloride and of delphinidin chloride 3'-methyl ether, possibly identical with petunidin chloride." J Chem Soc, Abstracts. 1930.
Brown et al., "Anti-IL-17 phase II data for psoriasis: a review." Journal of Dermatological Treatment 26.1 (2015): 32-36.
Busse et al., "Randomized, double-blind, placebo-controlled study of brodalumab, a human anti-IL-17 receptor monoclonal antibody, in moderate to severe asthma." American journal of respiratory and critical care medicine 188.11 (2013): 1294-1302.
Chebaane, Nouvelle synthèse d'aryl-2 naphtalenes et de binaphtyles réalisée au cours de l'aromatisation d'hydrobenzocoumarines. Diss. 1974.

(Continued)

*Primary Examiner* — Alicia L Otton
(74) *Attorney, Agent, or Firm* — Tarolli, Sundheim, Covell & Tummino LLP

(57) ABSTRACT

The present invention describes compounds according to formula I:

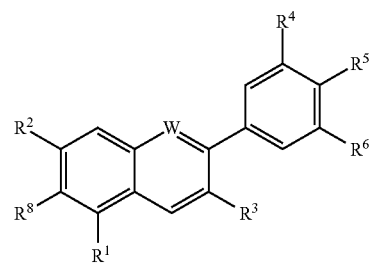

and compounds according to formula II:

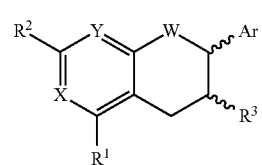

and additional related flavonoid compounds, as well as the use of the compounds in methods for the prevention or treatment of IL-17A-mediated disease in a subject.

6 Claims, 21 Drawing Sheets

(56) References Cited

OTHER PUBLICATIONS

Chesne et al., "Prime role of IL-17A in neutrophilia and airway smooth muscle contraction in a house dust mite-induced allergic asthma model." Journal of Allergy and Clinical Immunology 135.6 (2015): 1643.
Chense et al., "IL-17 in severe asthma. Where do we stand?." American journal of respiratory and critical care medicine 190.10 (2014): 1094-1101.
Ding et al., "Cyanidin-3-glucoside, a natural product derived from blackberry, exhibits chemopreventive and chemotherapeutic activity." Journal of Biological Chemistry 281.25 (2006): 17359-17368.
Gilman et al., "Some Quinolines Patterned as "Open Models" of Atabrine." Journal of the American Chemical Society 66.4 (1944): 621-625.
Gonzalez-Garcia et al., "IL-17 signaling-independent central nervous system autoimmunity is negatively regulated by TGF-β." The Journal of Immunology 182.5 (2009): 2665-2671.
Gu et al., "IL-17 family: cytokines, receptors and signaling." Cytokine 64.2 (2013): 477-485.
Harrington et al., "Interleukin 17-producing CD4+ effector T cells develop via a lineage distinct from the T helper type 1 and 2 lineages." Nature immunology 6.11 (2005): 1123-1132.
Hayashi, "Spektrographische Untersuchungen uber die Farbstoffe vom Benzopyryliumtypus. I. Uber die optischen Einflusse der Substitutionen an Seitenphenylgruppe." Acta Phytochim., Tokyo7 (1933): 117-141.
Kang et al., "Astrocyte-restricted ablation of interleukin-17-induced Act1-mediated signaling ameliorates autoimmune encephalomyelitis." Immunity 32.3 (2010): 414-425.
Kim et al., "Interleukin-17-producing innate lymphoid cells and the NLRP3 inflammasome facilitate obesity-associated airway hyperreactivity." Nature medicine 20.1 (2014): 54-61.
Lajoie et al., "Complement-mediated regulation of the IL-17A axis is a central genetic determinant of the severity of experimental allergic asthma." Nature immunology 11.10 (2010): 928-935.
Liu et al., "Crystal structures of interleukin 17A and its complex with IL-17 receptor A." Nature communications 4 (2013): 1888.
Miossec et al., "Targeting IL-17 and TH17 cells in chronic inflammation." Nature reviews Drug discovery 11.10 (2012): 763-776.
Nijveldt et al., "Flavonoids: a review of probable mechanisms of action and potential applications." The American journal of clinical nutrition 74.4 (2001): 418-425.
Porsbjerg et al., "Association of airway hyperresponsiveness with reduced quality of life in patients with moderate to severe asthma." Annals of Allergy, Asthma & Immunology 98.1 (2007): 44-50.
Robinson et al., "Clinical consequences of targeting IL-17 and TH17 in autoimmune and allergic disorders." Current allergy and asthma reports 13.6 (2013): 587-595.
Shay et al., "Molecular mechanisms and therapeutic effects of (−)-epicatechin and other polyphenols in cancer, inflammation, diabetes, and neurodegeneration." Oxid Med Cell Longev 2015 (2015): 181260.

Silverpil et al., "IL-17 in human asthma." Expert review of respiratory medicine 6.2 (2012): 173-186.
Hey et al., "Synthesis of 2-phenylnaphthalenes", Journal of the Chemical Society, Chemical Society, Jan. 1, 1940, pp. 374-383.
Swaidani et al., "The critical role of epithelial-derived Act1 in IL-17-and IL-25-mediated pulmonary inflammation." The Journal of Immunology 182.3 (2009): 1631-1640.
Wang et al., "The potential role of interleukin-17 in severe asthma." Current allergy and asthma reports 11.5 (2011): 388-394.
Witowski et al., "IL-17 stimulates intraperitoneal neutrophil infiltration through the release of GROα chemokine from mesothelial cells." The Journal of Immunology 165.10 (2000): 5814-5821.
Wright et al., "The human IL-17F/IL-17A heterodimeric cytokine signals through the IL-17RA/IL-17RC receptor complex." The Journal of Immunology 181.4 (2008): 2799-2805.
Zhang et al., "Supplementation of Cyanidin-3-O-β-Glucoside Promotes Endothelial Repair and Prevents Enhanced Atherogenesis in Diabetic Apolipoprotein E-Deficient Mice." The Journal of nutrition 143.8 (2013): 1248-1253.
PCT Invitation to Pay Additional Fees for PCT/US2015/048817, dated Nov. 5, 2015, pp. 1-10.
PCT International Search Report and Written Opinion for PCT/US2015/048817, dated Jan. 20, 2016, pp. 1-20.
Agache, Ioana, and Cezmi A. Akdis. "Endotypes of allergic diseases and asthma: an important step in building blocks for the future of precision medicine." Allergology International 65.3 (2016): 243-252.
Canonica, Giorgio W., et al. "Asthma: personalized and precision medicine." Current opinion in allergy and clinical immunology 18.1 (2018): 51-58.
Choy, David F., et al. "TH2 and TH17 inflammatory pathways are reciprocally regulated in asthma." Science translational medicine 7.301 (2015): 301ra129-301ra129.
Chung, Kian Fan, et al. "International ERS/ATS guidelines on definition, evaluation and treatment of severe asthma." European Respiratory Journal (2013): erj02020-2013.
Khokhlovich, Edward, et al. "Late Breaking Abstract—The biological pathways underlying response to anti-IL-17A (AIN457; secukinumab) therapy differ across severe asthmatic patients." (2017): OA2897.
Liu, Caini, et al. "The flavonoid cyanidin blocks binding of the cytokine interleukin-17A to the IL-17RA subunit to alleviate inflammation in vivo." Sci. Signal. 10.467 (2017): eaaf8823.
Lotvall, Jan, et al. "Asthma endotypes: a new approach to classification of disease entities within the asthma syndrome." Journal of Allergy and Clinical Immunology 127.2 (2011): 355-360.
Mukherjee, Manali, Sarah Svenningsen, and Parameswaran Nair. "Glucocortiosteroid subsensitivity and asthma severity." Current opinion in pulmonary medicine 23.1 (2017): 78-88.
Svenningsen, Sarah, and Parameswaran Nair. "Asthma endotypes and an Overview of Targeted Therapy for Asthma." Frontiers in medicine 4 (2017): 158.
Wenzel, Sally E. "Asthma phenotypes: the evolution from clinical to molecular approaches." Nature medicine 18.5 (2012): 716.

* cited by examiner

Specific Examples of A18 analogs

A

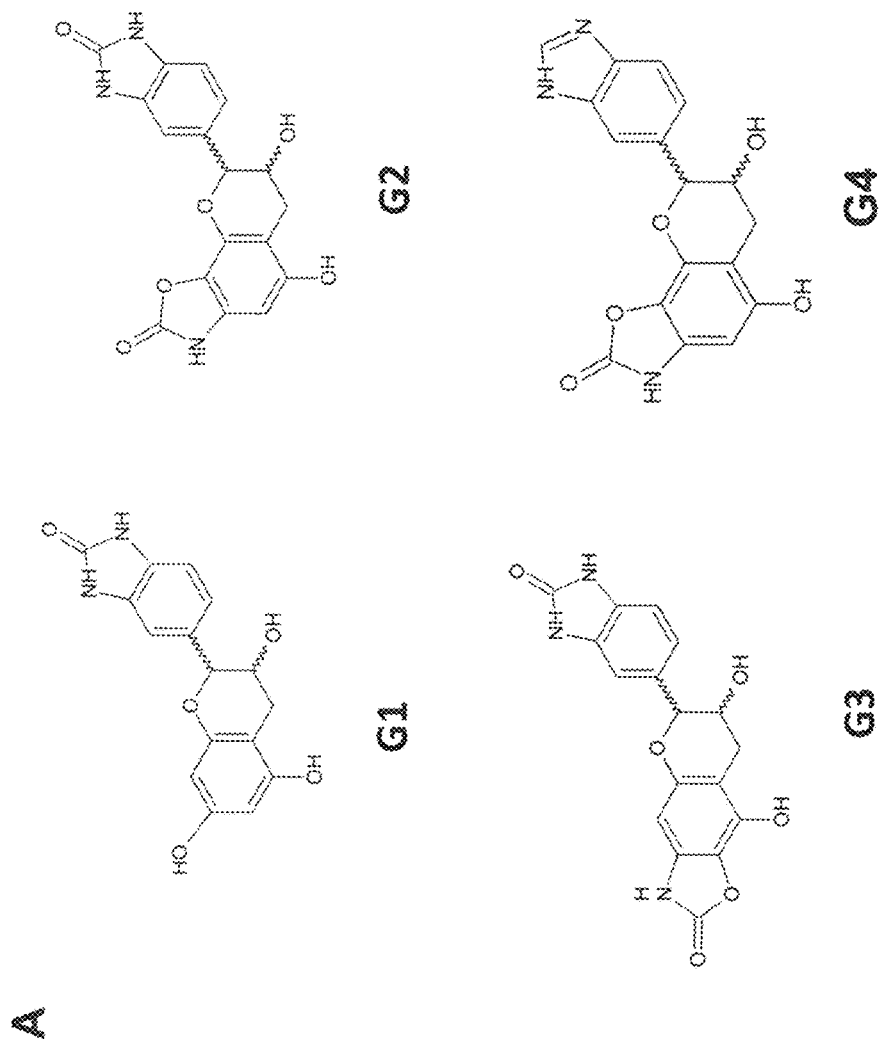
Figure 11 Specific Examples of A0 analogs

FLAVONOID IL-17A INHIBITORS

CROSS-REFERENCE TO RELATED APPLICATIONS

This application claims priority to U.S. Provisional Patent Application Ser. No. 62/046,243, filed Sep. 5, 2014, which is incorporated herein by reference.

GOVERNMENT FUNDING

This invention was made with government support under grant number NS071996awarded by the National Institutes of Health. The government has certain rights in this invention.

BACKGROUND

The interleukin-17 (IL-17) family consists of a subset of cytokines that participate in both acute and chronic inflammatory responses. Since the discovery of IL-17A (also called IL-17 or CTLA8) in 1993, five other members of this family IL-17B, IL-17C, IL-17D, IL-17E (also called IL-25), and IL-17F have been identified based on amino acid sequence homology. Notably, IL-17A is a pro-inflammatory cytokine produced by Th17 cells, a CD4+ T helper cell subset that has been shown to regulate tissue inflammatory responses. Recent studies indicate that IL-17A can also be produced by other cell types during inflammatory responses including CD8+ T cells, and γδ T cells, and innate lymphoid cells. Tremendous effort has been devoted to understand the function of IL-17A, demonstrating that that this pro-inflammatory cytokine plays a critical role in the pathogenesis of autoimmune diseases, metabolic disorders and cancer.

IL-17A signals through IL-17 receptor complex (IL-17RA and IL-17RC subunits) to transmit signals into cells. Wright, et al., Journal of immunology 181, 2799-2805 (2008). While the IL-17R adaptor protein Act1 interacts with TRAF6 and TRAF2/5 to induce transcriptional and post-transcriptional control of inflammatory gene expression, respectively, TRAF4 binds Act1 to promote ERK5 activation for cell proliferation. Bulek et al., Nat Immunol 12, 844-852, (2011). The main function of IL-17A is to coordinate local tissue inflammation via the upregulation of proinflammatory and neutrophil-mobilizing cytokines and chemokines (including IL-6, G-CSF, TNF-α, IL-1, CXCL1 (KC), CCL2 (MCP-1), CXCL2 (MIP-2)), as well as matrix metalloproteases to allow activated T cells to penetrate extracellular matrix. IL-17A has also been implicated in smooth muscle function and airway remodeling. Previous studies have suggested a central role for IL-17A in severe asthma and COPD (Al-Ramli et al., J Allergy Clin Immunol 123, 1185-1187 (2009)), those patients are typically unresponsive, or poorly responsive to currently available drugs. Indeed, high levels of IL-17A are found in induced sputum, bronchial biopsies and serum obtained from patients with severe asthma. Wang et al., Current allergy and asthma reports 11, 388-394 (2011). In addition, IL-17A levels were also increased in synovial fluids from arthritis patients, serum and brain tissue of multiple sclerosis patients, skin lesions of psoriasis patients, serum and tumor tissues of cancer patients. Gu et al., Cytokine 64, 477-485 (2013). Importantly, deficiency of IL-17A signaling components attenuated the pathogenesis of several autoimmune inflammatory diseases (such as allergen- and non-allergen-induced asthma, psoriasis, rheumatoid arthritis, multiple sclerosis) and tumorigenesis in animal models. Silverpil, E. & Linden, A., Expert review of respiratory medicine 6, 173-186, (2012). Thus, IL-17 pathway is a promising drug target for treatment of a wide spectrum of autoimmune inflammatory disorders and cancer.

Targeting IL-17A binding to IL-17RA has been reported to be an effective strategy for treating IL-17A-mediated autoimmune inflammatory diseases. Miossec, P. & Kolls, J. K., Nat Rev Drug Discov 11, 763-776 (2012). Monoclonal neutralizing antibodies against IL-17A has been developed as drug candidates for IL-17A inhibition. Brown et al., The Journal of dermatological treatment 26, 32-36 (2015). Preclinical studies have yielded promising results in murine models of allergic lung diseases. Lajoie et al., Nature immunology 11, 928-935 (2010). Clinical trials with these antibodies have shown promising results with IL-17A-mediated inflammatory diseases, including asthma, psoriasis, rheumatoid arthritis, ankylosing spondylitis and multiple sclerosis. Robinson et al., Current allergy and asthma reports 13, 587-595 (2013). Anti-IL17A antibody (Cosentyx/secukinumab from Novartis) was approved by FDA (January 2015) for the treatment of psoriasis and is currently on 50 clinical trials for various autoimmune diseases including asthma. Extreme efficacy (greater than 85% responding rate) was observed for psoriasis. Other anti-IL-17 antibodies (Ixekizumab from Eli Lily and MSB0010841 from Merck) are also in active clinical trials. However, given the considerable cost for antibody production and limitation for administration (only through intravenous route), it is advantageous to develop cost-effective alternatives such as small molecule drugs for IL-17A inhibition.

SUMMARY OF THE INVENTION

The inventors performed computer-aided docking-based virtual screening for small molecule inhibitors that have the potential to disrupt IL-17A-IL-17RA interaction by using the structural information of IL-17RA. Two small molecule lead compounds (A18 and A0) were identified that exhibited excellent ability to inhibit IL-17A binding to IL-17RA in an in vitro biochemical assay. Experimental evidence was obtained that A18 effectively inhibited IL-17A-induced intraperineal neutrophilia; attenuated IL-17A-dependent airway inflammation and hyperreactivity (AHR) in mouse model of severe asthma; ablated IL-17A-mediated experimental autoimmune encephalomyelitis (EAE) induced by Th17 adoptive transfer; reduced IL-17A-induced skin hyperplasia and melanoma metastasis. Two basic A18-derived structural skeletons were defined that are critical for the inhibition of IL-17A-IL-17RA binding. These two basic skeletons served as prototypes for developing small molecule drug candidates for treating IL-17A-mediated diseases.

Accordingly, the present invention provides compounds according to formula I:

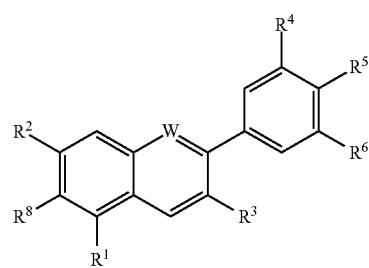

and compounds according to formula II:

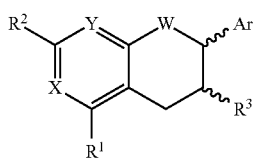

and additional related flavonoid compounds, as well as the use of the compounds in methods for the prevention or treatment of IL-17A-mediated disease in a subject. Examples of IL-17A-mediated diseases include cancer, autoimmune disease, and inflammatory disease.

BRIEF DESCRIPTION OF THE FIGURES

The present invention may be more readily understood by reference to the following figures, wherein.

Figure 6:
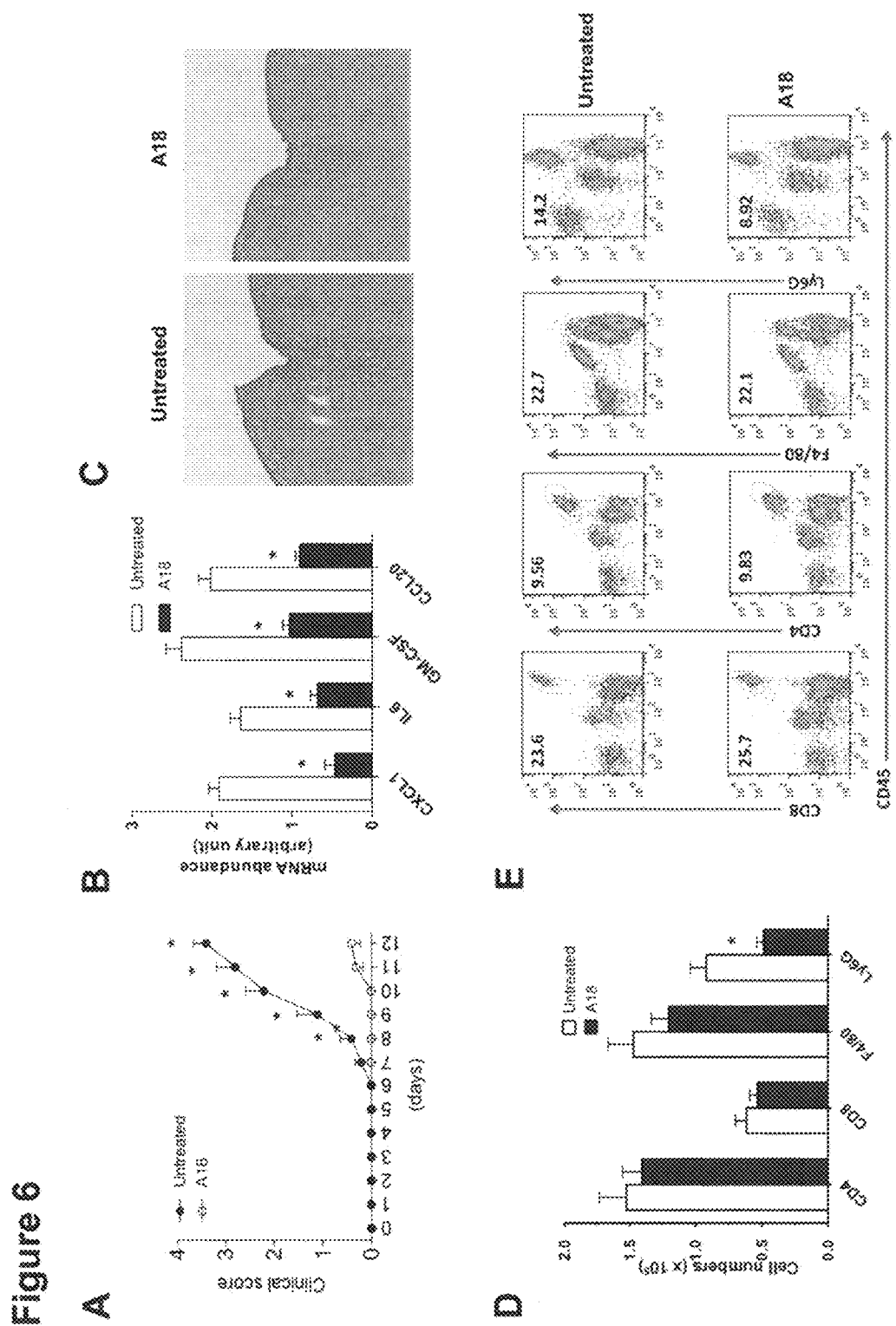

FIG. 6 (A-E) provides graphs and images showing A18 inhibited Th17-mediated experimental allergic encephalomyelitis (EAE) in mice. Primed MOG-33-55 specific WT T cells (10 days) were re-stimulated with MOG 35-55 in vitro in the presence of recombinant IL-23 for 5 days and then transferred to naive 10-week WT C57BL/6J female mice treated with or without A18 (30 μg per mouse). Mice were sacrificed after 12 days of onset of diseases. A. Mean clinical score of EAE in untreated and A18-treated mice after Th17 cell transfer. B. Real-time PCR for the expression of IL-17 target genes of the spinal cords from untreated and A18-treated mice. C. H&E staining of the spinal cords of from untreated and A18-treated mice. D-E. Immune cell infiltration in the brains from untreated and A18-treated mice was analyzed by flow cytometry. Error bar, SEM; n=5 per group. *P<0.05. This is representative data of three repeated experiments.

Figure 7:
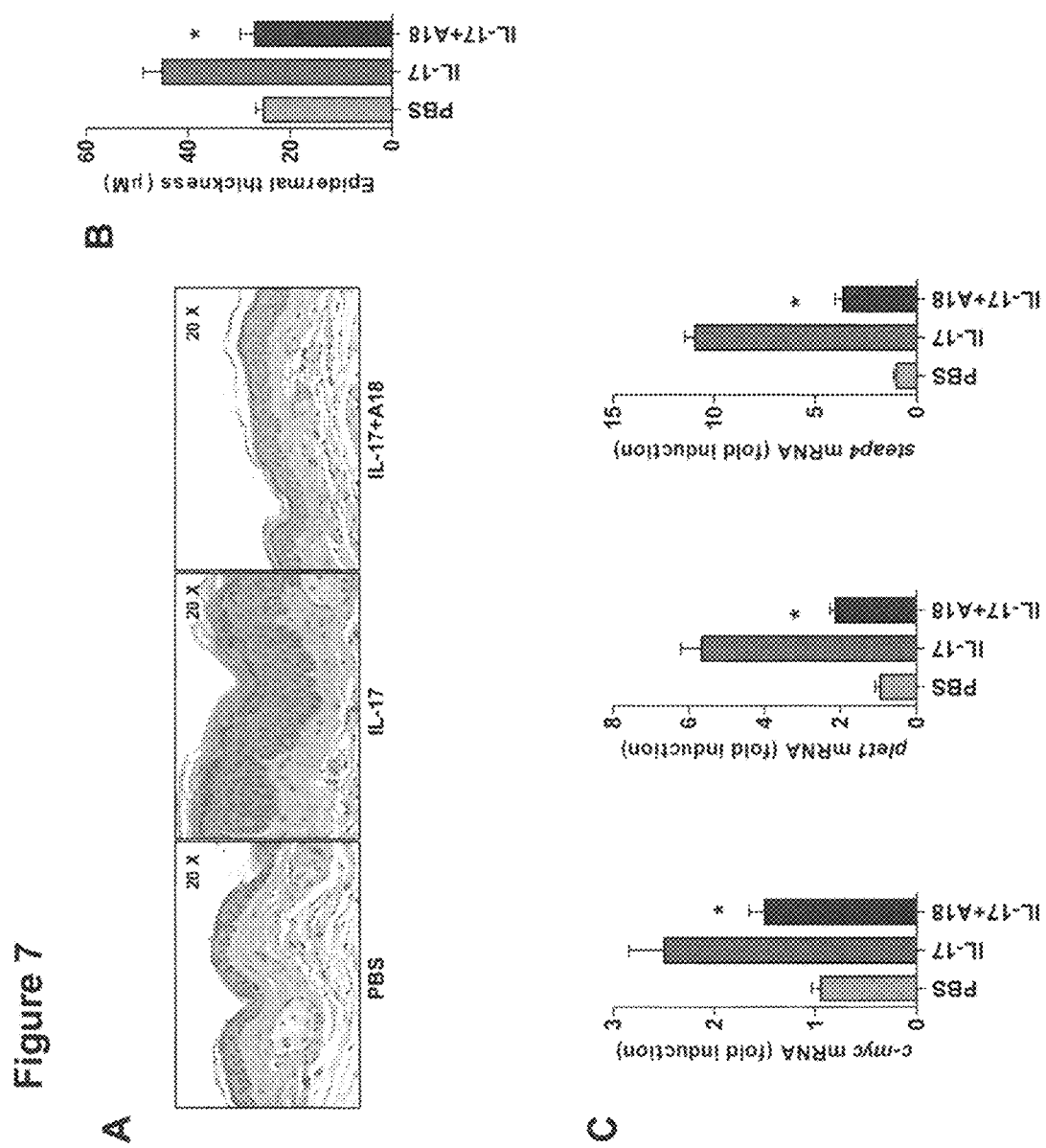
Figure 7:
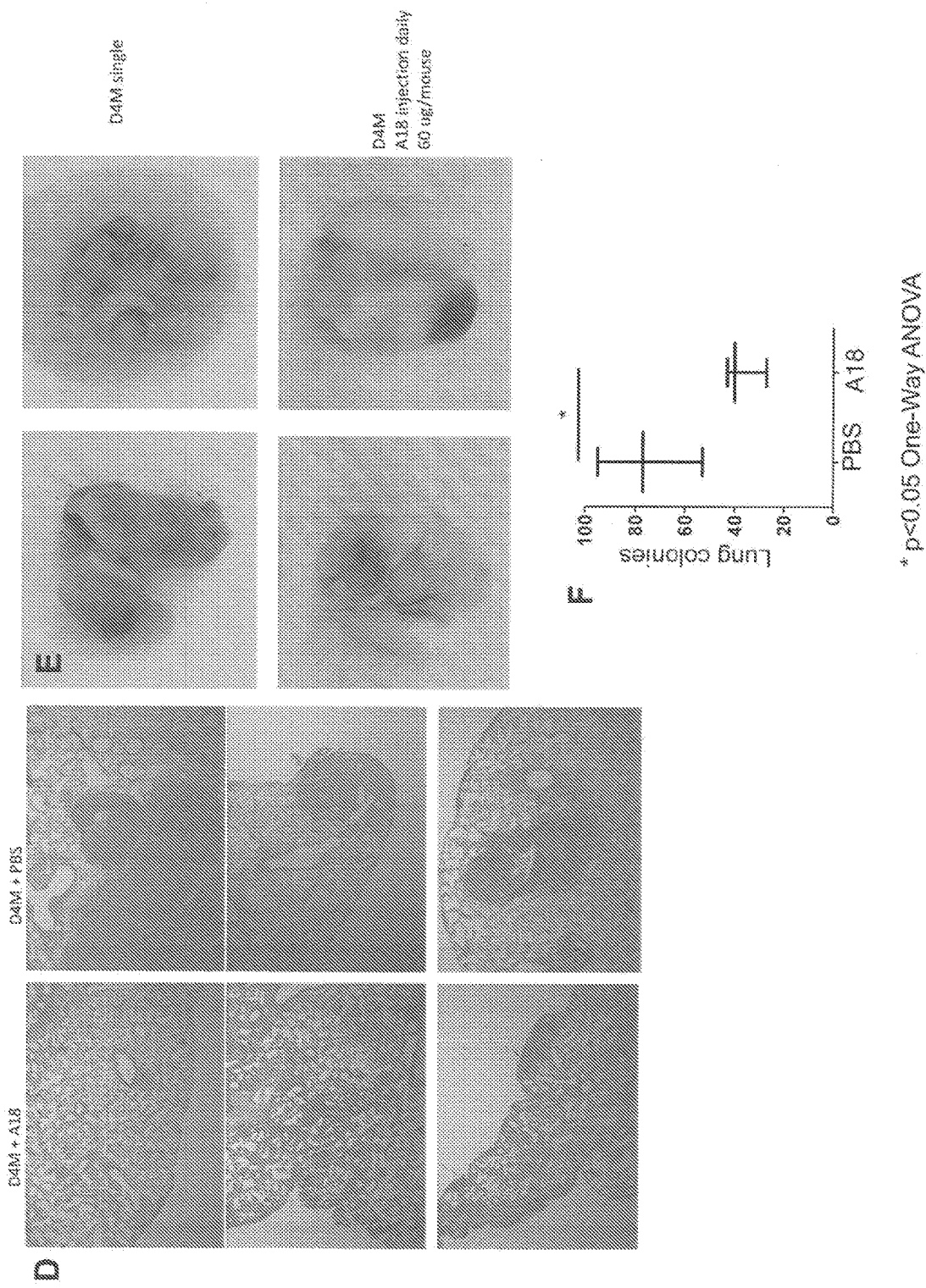

FIG. 7 (A-F) provides graphs and images showing A18 inhibited IL-17-induced skin epidermal hyperplasia and reduced experimental melanoma lung metastasis in mice. A-C. The ears of 8-week WT C57BL/6J female were each injected intradermally every day with 500 ng of IL-17A with or without A18 (30 μg per mouse). On day 6, ears were collected for staining with H&E (A). Graph represents epidermal thickness (B). C. Real-time PCR for the expression of IL-17A target genes of the skin samples from the mice. Error bar, SEM; n=5 per group. *P<0.05. D-E. A total of $10^6$ D4M melanoma cells were injected into C57BL/6 each mouse through tail vein. Mice were injected with PBS (D4M+PBS) or A18 (D4M+A18, 60 μg per mouse) daily. On day 20, lung tissue was collected for H&E staining (D); E. tumors on lung surface (marked by arrows); F. total tumor numbers were counted.

Figure 8:
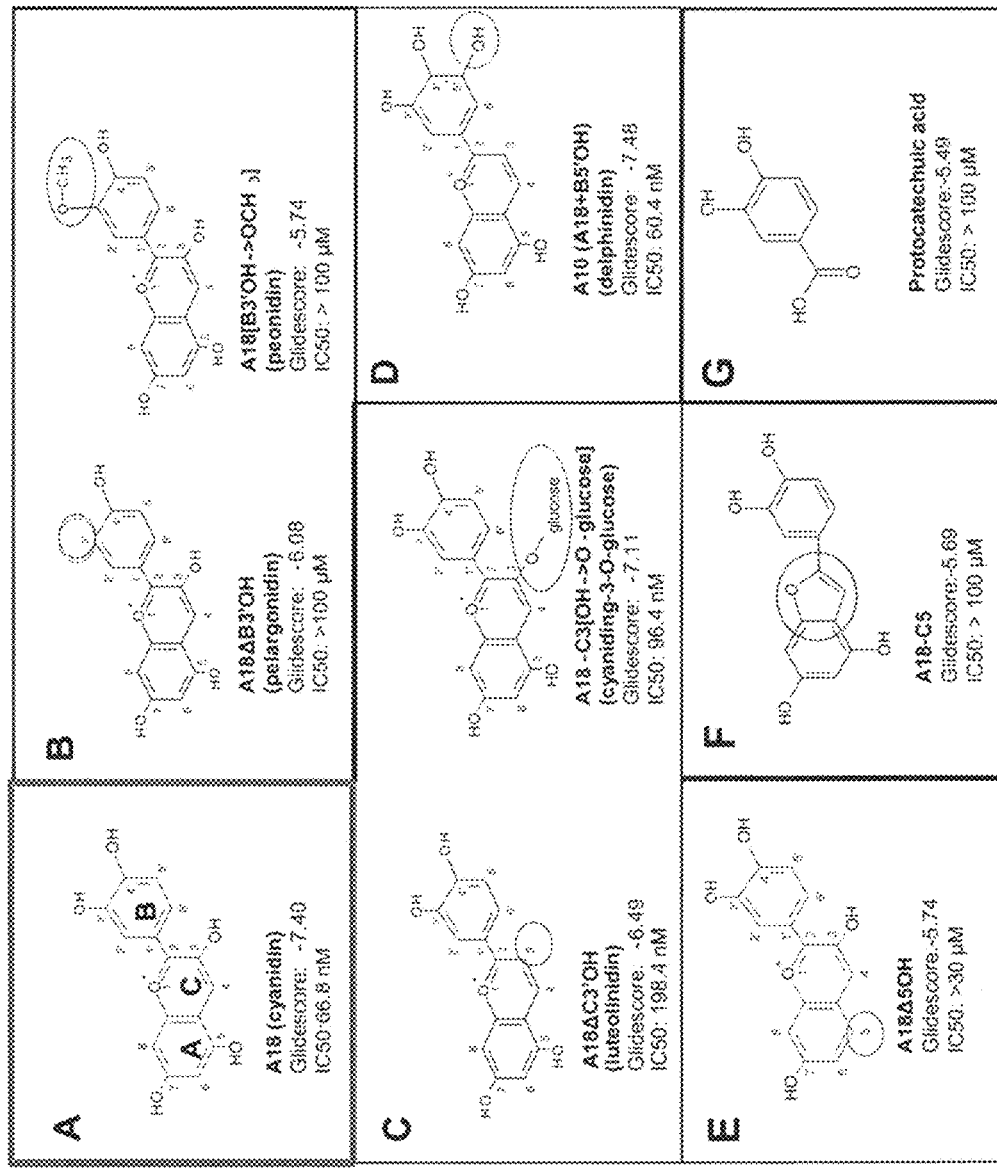

FIG. 8 provides chemical schemes showing the characterization of critical chemical groups of A18 for IL-17A-IL-17RA binding. A-F. Shown are the compounds that are structurally related to A18. G. A18 discomposed product, protocatechuic acid.

Figure 9:
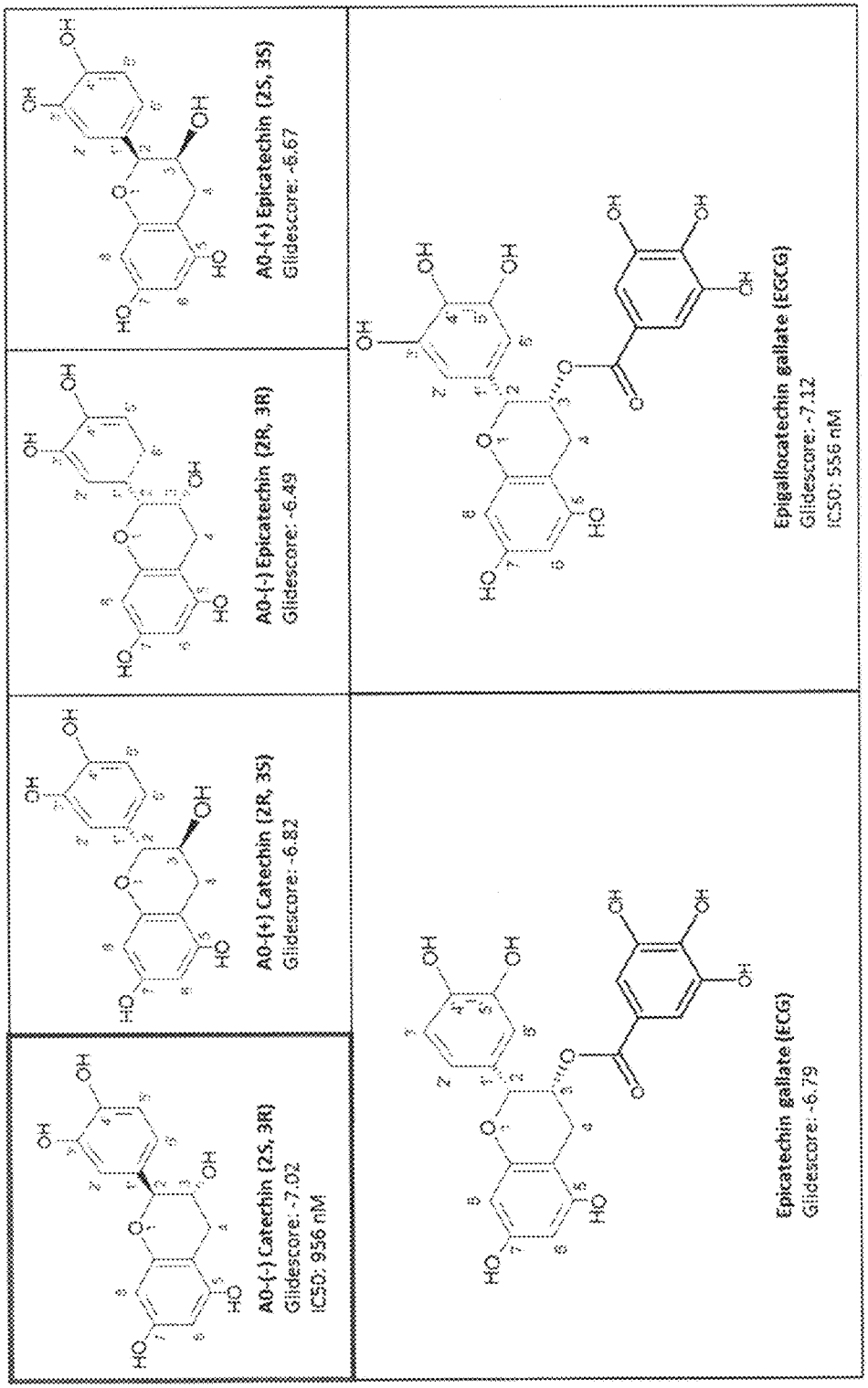

FIG. 9 provides chemical schemes showing catechin and related compounds in inhibition of IL-17A binding to IL-17RA.

Figure 10:
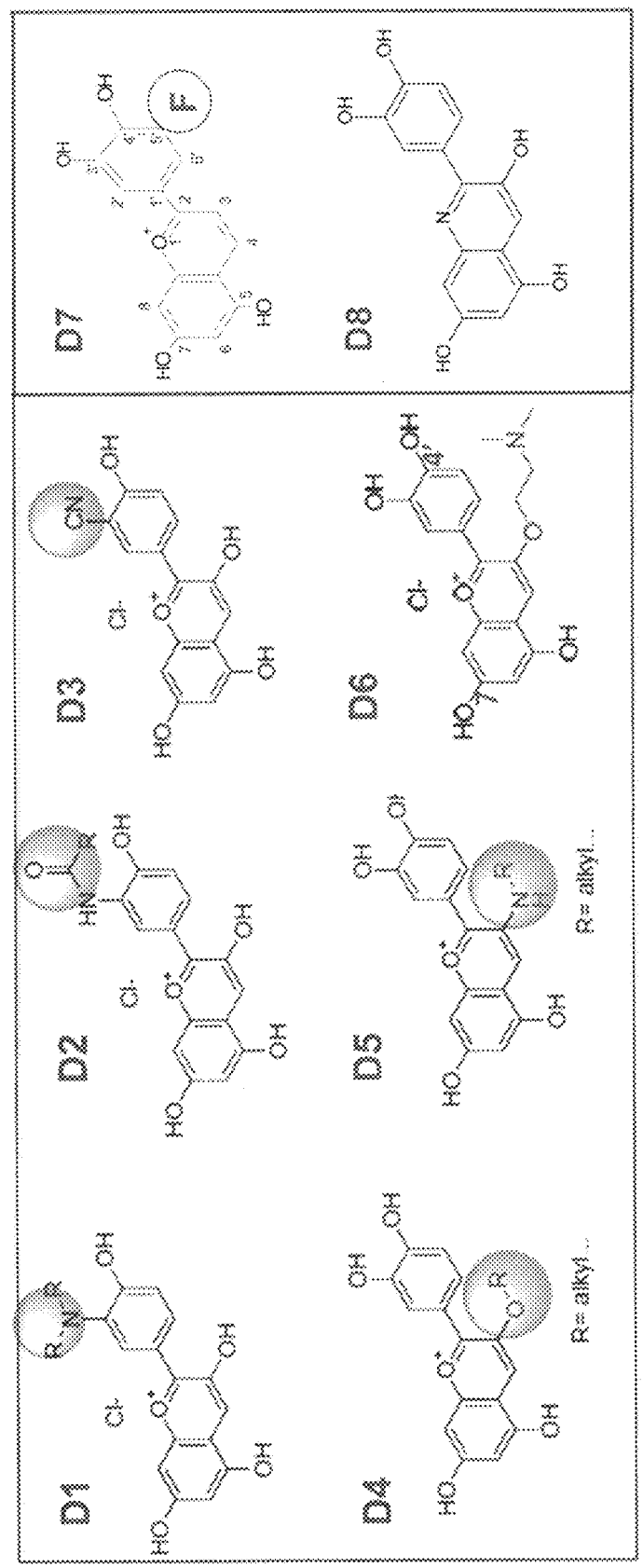
Figure 10B:
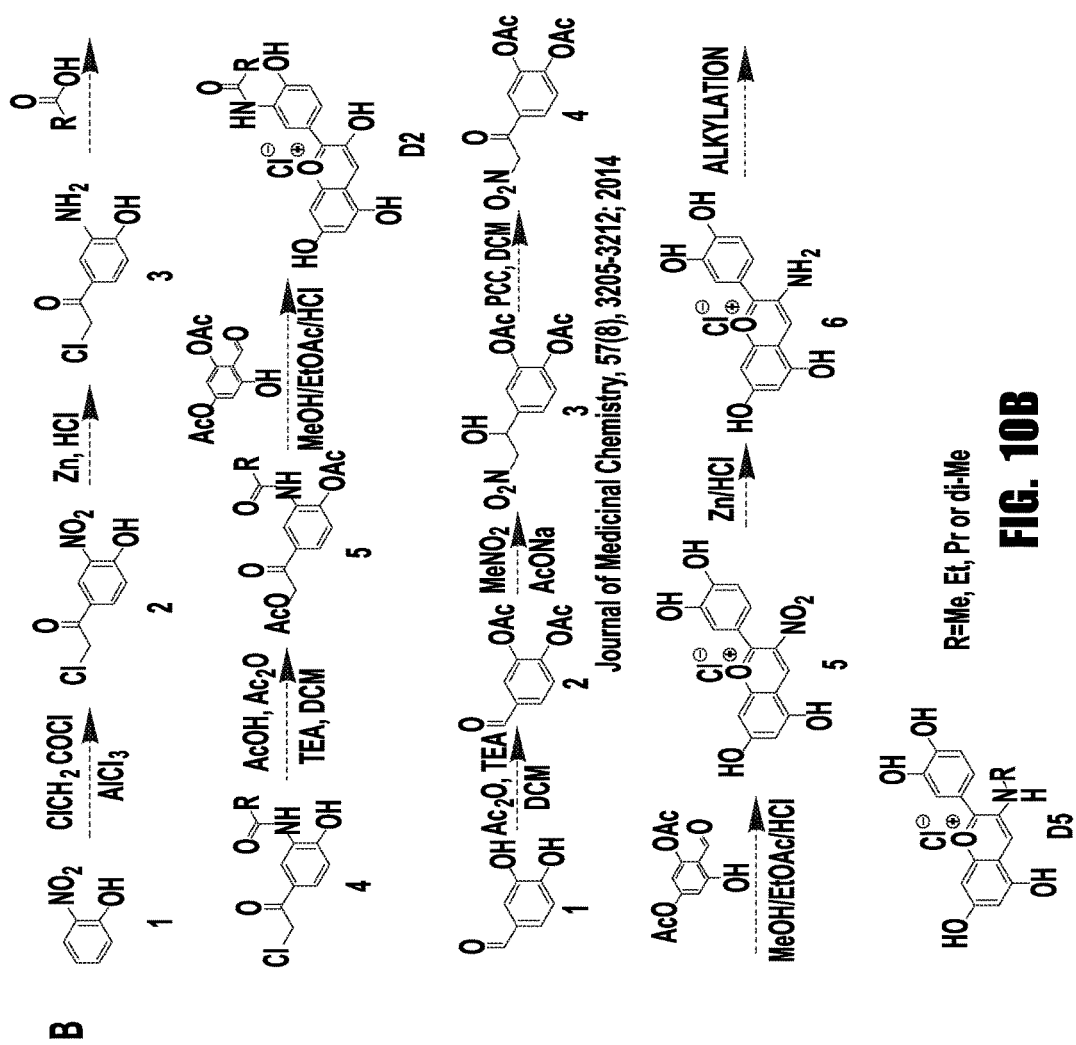
Figure 10C:
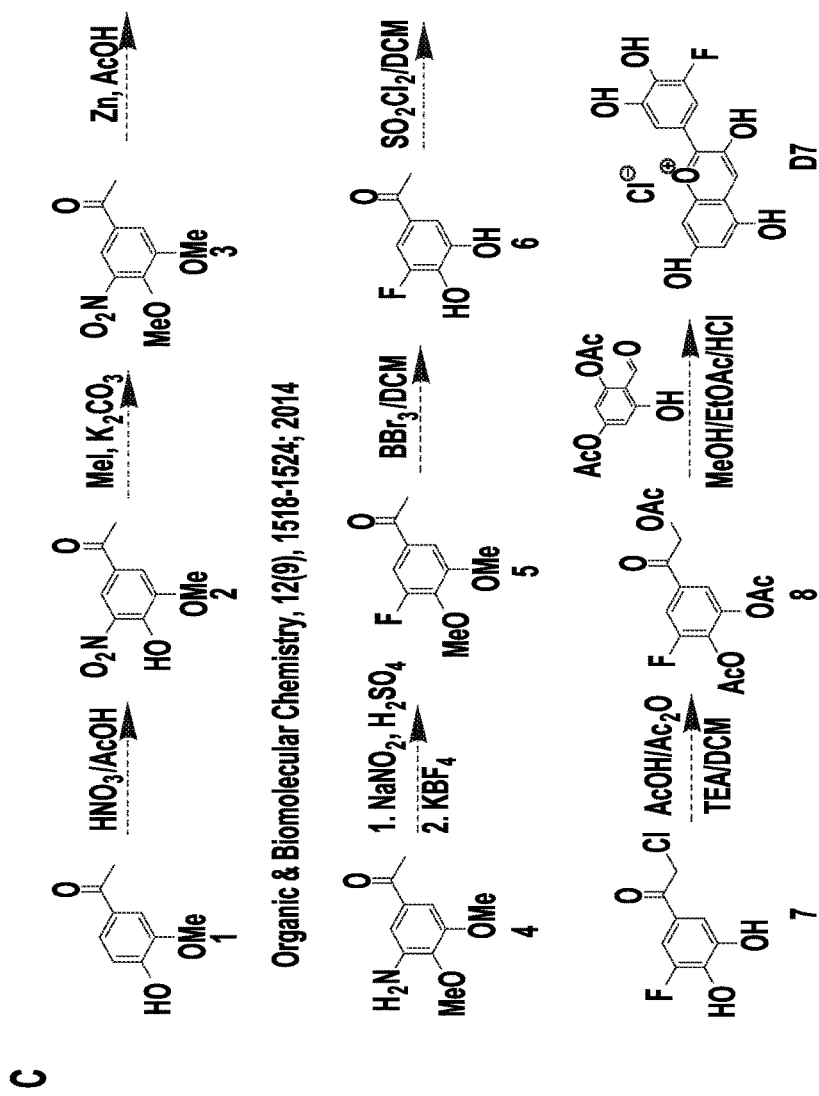

FIG. 10 (A-D) provides chemical schemes showing specific examples of A18 analogs. (A) D1-7: Substitution of hydroxyl groups to improve stability, potency and solubility. D8: Modification of the ring structure to improve stability and potency. (B-D) Synthesis routes of D2, D5, D7 and D8.

FIG. 11 (A-E) provides chemical schemes showing specific examples of A0 analogs. (A) G1, an example for Formula II of A0 analogs; G2 and G4, examples of Formula IV of A0 analogs; G3, an example of Formula V of A0 analogs. (B-E) Synthesis routes of G1-G4.

DETAILED DESCRIPTION OF THE INVENTION

The inventors have demonstrated herein that compounds according to formulas I-V exhibit higher potency and/or selectivity as IL-17A inhibitors, and can also be used to treat IL-17A-mediated diseases such as multiple sclerosis.

DEFINITIONS

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

As used herein, the term "organic group" is used to mean a hydrocarbon group that is classified as an aliphatic group, cyclic group, or combination of aliphatic and cyclic groups (e.g., alkaryl and aralkyl groups). An alkaryl group is a an aryl group that is attached to the remainder of the structure by an intervening alkyl group, whereas an aralkyl group is an aryl group that is attached directly to the structure but that includes one or more additional alkyl groups attached thereto. In the context of the present invention, suitable organic groups for compounds of this invention are those that do not interfere with the IL-17A inhibiting activity of the compounds. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Alkyl groups including 4 or fewer carbon atoms can also be referred to as lower alkyl groups. Alkyl groups can also be referred to by the number of carbon atoms that they include (i.e., $C_1$-$C_4$ alkyl groups are alky groups including 1-4 carbon atoms).

Cycloalkyl, as used herein, refers to an alkyl group (i.e., an alkyl, alkenyl, or alkynyl group) that forms a ring structure. Cyclic groups can be monocyclic or polycyclic and preferably have from 3 to 10 ring carbon atoms. A cycloalkyl group can be attached to the main structure via an alkyl group including 4 or less carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halo moieties include chlorine, bromine, fluorine, and iodine.

The term "aryl" as used herein includes carbocyclic aromatic rings or ring systems. The aryl groups may include a single aromatic ring, a plurality of separate aromatic rings, or a fused aromatic ring system. Carbocyclic aromatic rings do not include heteroatoms. Examples of aryl groups include phenyl, naphthyl, biphenyl, fluorenyl and indenyl. Aryl groups may be substituted or unsubstituted.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The terms "arylene" and "heteroarylene" are the divalent forms of the "aryl" and "heteroaryl" groups defined above. The terms "arylenyl" and "heteroarylenyl" are used when "arylene" and "heteroarylene", respectively, are substituted. For example, an alkylarylenyl group comprises an arylene moiety to which an alkyl group is attached.

The term "fused aryl group" includes fused carbocyclic aromatic rings or ring systems. Fused aryl groups include a plurality of aromatic rings that are fused to form a single aromatic system. Examples of fused aryl groups include naphthalene ($C_{10}$), anthracene ($C_{14}$), phenanthrene ($C_{14}$) and pyrene ($C_{16}$) fused aryl groups. Collectively, fused aryl groups can be referred to by reference to the number of carbon ring atoms they contain; i.e., a $C_{10}$-$C_{18}$ carboaryl group. The number of rings included in the fused group can be indicated using the terms bicyclic, tricyclic, etc. For example, a bicyclic fused aryl group includes two aryl rings.

The term "fused cycloalkyl aryl group" includes a ring system including both cycloalkyl and aromatic rings that are fused to form a single ring system. A "fused heterocycloalkyl aryl group" is a ring system that includes both a heterocycloalkyl ring and an aromatic ring that are fused to form a single ring system.

When a group is present more than once in any formula or scheme described herein, each group (or substituent) is independently selected, whether explicitly stated or not. For example, for the formula —C(O)—NR$_2$ each R group is independently selected.

The terms ester, amide, amine, hydroxyl, sulfonate, phosphonate, and guanidine refer to various different functional groups that may be included in compounds of the invention. The functional groups are attached to a carbon atom that forms part of an organic substituent. The functional groups are further described by the following chemical formulas: ester=R—(CO)—O—R; amide=R—(CO)—NH—R; amine=R—NH$_2$, hydroxyl=R—OH; sulfonate=R—O—SO$_3^-$, where R represents the alkyl or aromatic group(s) to which the functional group is attached. Further examples of functional groups are provided below.

Acylamido (acylamino): —NR$^1$C(=O)R$^2$, wherein R$^1$ is an amide substituent, for example, hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. Acylamido groups can be substituted; for example, the acylamido groups can be amine substituted acylamido groups having the formula —NH—CO—(CH$_2$)$_x$—NH$_2$, wherein x is an integer from 1-4.

Ureido: —N(R$^1$)CONR$^2$R$^3$ wherein R$^2$ and R$^3$ are independently amino substituents, as defined for amino groups, and R$^1$ is a ureido substituent, for example, hydrogen or a $C_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, —NMeCONEt$_2$ and —NHC(=O)NHPh.

Sulfonyl (sulfone): —S(=O)$_2$R, wherein R is a sulfone substituent, for example, a $C_{1-7}$ alkyl group or a $C_{5-20}$ aryl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl). The sulfone substituent may in some cases be an amino group, as defined above. These groups may be termed "aminosulfonyl" groups.

Sulfonamino: —NR$^1$S(=O)$_2$R, wherein R$^1$ is an amino substituent, as defined for amino groups, and R is a sulfonamino substituent, for example, a $C_{1-7}$ alkyl group or a $C_{5-20}$ aryl group. Examples of sulfonamino groups include, but are not limited to, —NHS(=O)$_2$CH$_3$, —NHS(=O)$_2$Ph and —N(CH$_3$)S(=O)$_2$C$_6$H$_5$.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with one or more nonperoxidic O, N, S, or F substituents or other conventional substituents such as methyl groups. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, cyanoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

"Treat", "treating", and "treatment", etc., as used herein, refer to any action providing a benefit to a subject afflicted with an IL-17A-mediated condition or disease such as multiple sclerosis, including improvement in the condition through lessening or suppression of at least one symptom, delay in progression of the disease, etc.

Prevention, as used herein, refers to any action providing a benefit to a subject at risk of being afflicted with an IL-17A-mediated condition or disease such as multiple sclerosis, including avoidance of the development of the condition or disease or a decrease of one or more symptoms of the disease should a disease develop. The subject may be at risk as a result of family history.

"Pharmaceutically acceptable" as used herein means that the compound or composition is suitable for administration to a subject for the methods described herein, without unduly deleterious side effects in light of the severity of the disease and necessity of the treatment.

The term "therapeutically effective" is intended to qualify the amount of each agent which will achieve the goal of decreasing disease severity while avoiding adverse side effects such as those typically associated with alternative therapies. The therapeutically effective amount may be administered in one or more doses. An effective dose, on the other hand, is an amount sufficient to provide a certain effect, such as enzyme inhibition, but may or may not be therapeutically effective.

Flavonoid IL-17A Inhibitors

One aspect of the invention provides a compound having a formula according to formula I:

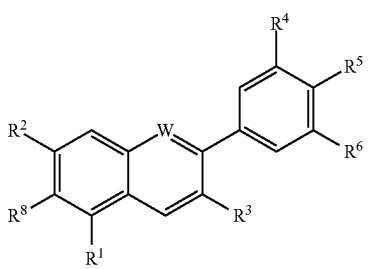

I wherein $R^3$, $R^6$, and $R^8$ are independently selected from —H, —OH, halogen, —$C_1$-$C_6$-alkyl, —$C_1$-$C_6$-cycloalkyl, aryl, heteroaryl, —CN, —$SO_2$—$C_1$-$C_4$-alkyl, —$SO_2$(NH)—$C_1$-$C_4$-alkyl, —$CF_3$, —$OCHF_2$, —$OCF_3$, —O—$C_1$-$C_6$-alkyl, —O—$C_1$-$C_6$-cycloalkyl, —$OCH_2CH_2$—O—$C_1$-$C_4$-alkyl, —$SCF_3$, —$SO_3CF_3$, —$SF_5$, —$CONH_2$, —CONH—$C_1$-$C_4$-alkyl, —CON($C_1$-$C_4$-alkyl)$_2$; $R^1$, $R^2$, $R^4$, and $R^5$ are independently selected from —H, —OH, —O—$C_1$-$C_6$-alkyl, —O—$C_1$-$C_6$-cycloalkyl, halogen, —$NH_2$, —NH—$C_1$-$C_6$-alkyl, —N($C_1$-$C_6$-alkyl)$_2$, —NH—CO—$C_1$-$C_6$-alkyl, —$NHSO_2$—$C_1$-$C_6$-alkyl, —$NHSO_2$N($C_1$-$C_6$-alkyl)$_2$, —NHCONH—$C_1$-$C_6$-alkyl, —NHCON($C_1$-$C_6$-alkyl)$_2$, —NH-aryl; and wherein W is selected from the group consisting of —CH—, —$O^+$—, and —N—; or a pharmaceutically acceptable salt thereof.

In some embodiments, at least one of $R^1$, $R^2$, $R^4$, and $R^5$ of the compound of formula I is selected from the group consisting of —O—$C_1$-$C_6$-alkyl, —O—$C_1$-$C_6$-cycloalkyl, halogen, —$NH_2$, —NH—$C_1$-$C_6$-alkyl, —N($C_1$-$C_6$-alkyl)$_2$, —NH—CO—($C_1$-$C_6$-alkyl), —$NHSO_2$—$C_1$-$C_6$-alkyl, —$NHSO_2$N($C_1$-$C_6$-alkyl)$_2$, —NHCONH—$C_1$-$C_6$-alkyl, —NHCON($C_1$-$C_6$-alkyl)$_2$, and —NH-aryl, while in further embodiments of the compounds of formula I, W is selected from —CH— and —N—.

Another aspect of the invention provides a compound according to formula II:

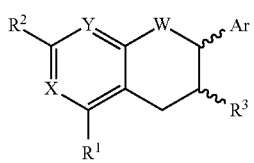

II

X and Y are independently —CH— or —N—; W is —$CH_2$—, —NH—, or —O—; $R^1$ and $R^2$ are independently selected from —H, —OH, —O—$C_1$-$C_6$-alkyl, —O—$C_1$-$C_6$-cycloalkyl, halogen, —$NH_2$, —NH—$C_1$-$C_6$-alkyl, —N($C_1$-$C_6$-alkyl)$_2$, —NH—CO—$C_1$-$C_6$-alkyl, —$NHSO_2$—$C_1$-$C_6$-alkyl, —$NHSO_2$N($C_1$-$C_6$-alkyl)$_2$, —NHCONH—$C_1$-$C_6$-alkyl, —NHCON($C_1$-$C_6$-alkyl)$_2$, —NH-heteroaryl, —NH-aryl; $R^3$ is selected from —H, —OH, halogen, —$C_1$-$C_6$-alkyl, $C_1$-$C_6$-cycloalkyl, aryl, heteroaryl, —$SO_2$—$C_1$-$C_4$-alkyl, —$SO_2$(NH)—$C_1$-$C_4$-alkyl, —$CF_3$, —O—$C_1$-$C_6$-alkyl, —O—$C_1$-$C_6$-cycloalkyl, —$OCH_2CH_2$—O—$C_1$-$C_4$-alkyl, —$SO_3CF_3$, —$CONH_2$, —CONH—$C_1$-$C_4$-alkyl, —CONH($C_1$-$C_4$-alkyl)$_2$; and Ar is an aryl, heteroaryl, bicyclic fused aryl, bicyclic fused heteroaryl group, bicyclic fused cycloalkyl aryl group, or bicyclic fused heterocycloalkyl aryl group; or a pharmaceutically acceptable salt thereof.

In some embodiments, Ar is an aryl group according to formula III:

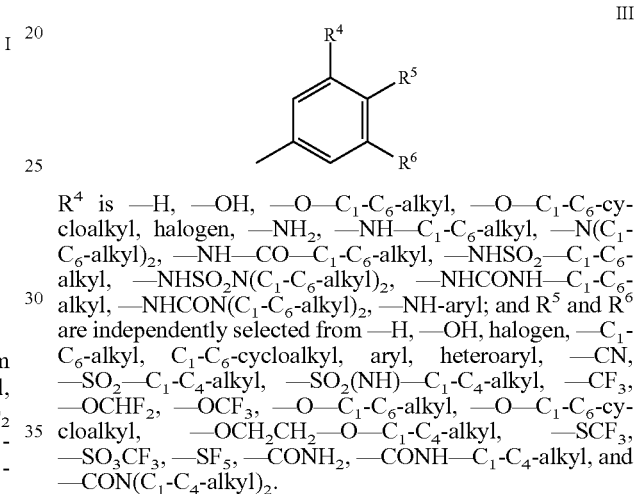

III $R^4$ is —H, —OH, —O—$C_1$-$C_6$-alkyl, —O—$C_1$-$C_6$-cycloalkyl, halogen, —$NH_2$, —NH—$C_1$-$C_6$-alkyl, —N($C_1$-$C_6$-alkyl)$_2$, —NH—CO—$C_1$-$C_6$-alkyl, —$NHSO_2$—$C_1$-$C_6$-alkyl, —$NHSO_2$N($C_1$-$C_6$-alkyl)$_2$, —NHCONH—$C_1$-$C_6$-alkyl, —NHCON($C_1$-$C_6$-alkyl)$_2$, —NH-aryl; and $R^5$ and $R^6$ are independently selected from —H, —OH, halogen, —$C_1$-$C_6$-alkyl, $C_1$-$C_6$-cycloalkyl, aryl, heteroaryl, —CN, —$SO_2$—$C_1$-$C_4$-alkyl, —$SO_2$(NH)—$C_1$-$C_4$-alkyl, —$CF_3$, —$OCHF_2$, —$OCF_3$, —O—$C_1$-$C_6$-alkyl, —O—$C_1$-$C_6$-cycloalkyl, —$OCH_2CH_2$—O—$C_1$-$C_4$-alkyl, —$SCF_3$, —$SO_3CF_3$, —$SF_5$, —$CONH_2$, —CONH—$C_1$-$C_4$-alkyl, and —CON($C_1$-$C_4$-alkyl)$_2$.

In other embodiments, Ar is a bicyclic fused heteroaryl group or a bicyclic fused heterocycloalkyl aryl group. For example, in some embodiments Ar is selected from the group consisting of:

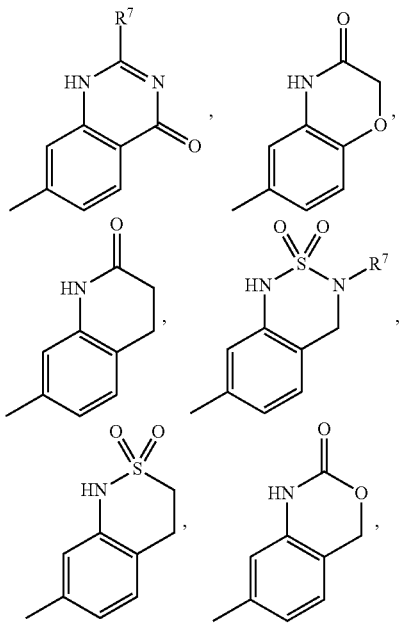

-continued

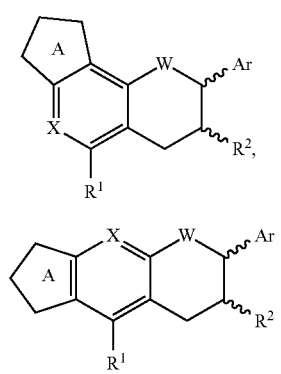

wherein R⁷ is —H or —C₁-C₆-alkyl.

In additional embodiments, at least one of R¹, R², R⁴, and R⁵ is selected from the group consisting of —O—C₁-C₆-alkyl, —O—C₁-C₆-cycloalkyl, halogen, —NH₂, —NH—C₁-C₆-alkyl, —N(C₁-C₆-alkyl)₂, —NH—CO—C₁-C₆-alkyl, —NHSO₂—C₁-C₆-alkyl, —NHSO₂N(C₁-C₆-alkyl)₂, —NHCONH—C₁-C₆-alkyl, —NHCON(C₁-C₆-alkyl)₂, and —NH-aryl. In further embodiments of the compounds of formula II, W is —CH₂—, while in yet further embodiments X and Y are —CH—.

Another aspect of the invention provides a compound according to formula IV or V:

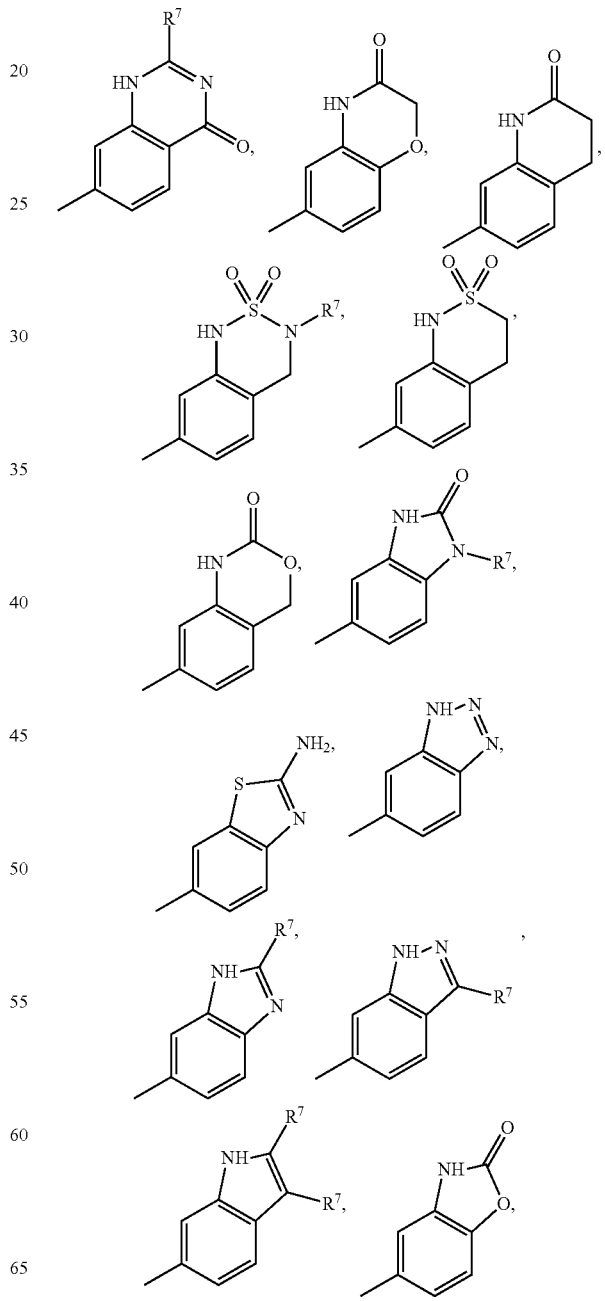

wherein X is —CH— or —N—; W is —CH₂—, —NH—, or —O—; Ring A is a heterocyclic 5-membered ring; R¹ is selected from —H, —OH, —O—C₁-C₆-alkyl, —O—C₁-C₆-cycloalkyl, halogen, —NH₂, —NH—C₁-C₆-alkyl, —N(C₁-C₆-alkyl)₂, —NH—CO—C₁-C₆-alkyl, —NHSO₂—C₁-C₆-alkyl, —NHSO₂N(C₁-C₆-alkyl)₂, —NHCONH—C₁-C₆-alkyl, —NHCON(C₁-C₆-alkyl)₂, —NH-heteroaryl, —NH-aryl; R² is selected from —H, —OH, halogen, —C₁-C₆-alkyl, C₁-C₆-cycloalkyl, aryl, heteroaryl, —SO₂—C₁-C₄-alkyl, —SO₂(NH)—C₁-C₄-alkyl, —CF₃, —O—C₁-C₆-alkyl, —O—C₁-C₆-cycloalkyl, —OCH₂CH₂—O—C₁-C₄-alkyl, —SO₃CF₃, —CONH₂, —CONH—C₁-C₄-alkyl, —CON(C₁-C₄-alkyl)₂; and Ar is an aryl, heteroaryl, bicyclic fused aryl, bicyclic fused heteroaryl group, bicyclic fused cycloalkyl aryl group, bicyclic fused heterocycloalkyl aryl group; or a pharmaceutically acceptable salt thereof.

In some embodiments, Ar is a bicyclic fused heteroaryl group or a bicyclic fused heterocycloalkyl aryl group. For example, in some embodiments Ar is selected from the group consisting of:

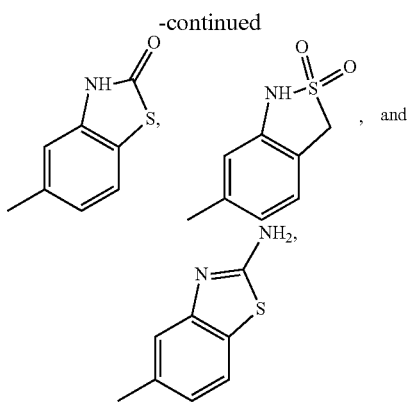

wherein $R^7$ is —H or —$C_1$-$C_6$-alkyl.

A variety of different 5-membered heterocyclic rings can be provided at ring A. For example, in some embodiments, ring A is selected from the group consisting of:

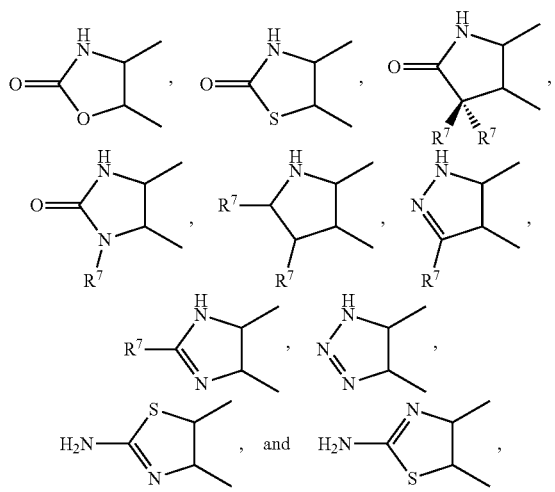

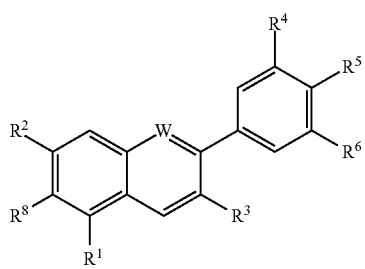

wherein $R^7$ is —H or —$C_1$-$C_6$-alkyl. In further embodiments of the compounds of formula IV and V, W is —O—.

Treatment of IL-17A-Mediated Disease Using Flavonoid Compounds of Formulas I-V.

Another aspect of the invention provides a method of treating an IL-17A-mediated disease in a subject, by administering to the subject a therapeutically effective amount of a compound according to formula I:

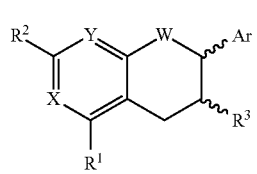

wherein $R^3$, $R^6$, and $R^8$ are independently selected from —H, —OH, halogen, —$C_1$-$C_6$-alkyl, —$C_1$-$C_6$-cycloalkyl, aryl, heteroaryl, —CN, —$SO_2$—$C_1$-$C_4$-alkyl, —$SO_2$(NH)—$C_1$-$C_4$-alkyl, —$CF_3$, —$OCHF_2$, —$OCF_3$, —O—$C_1$-$C_6$-alkyl, —O—$C_1$-$C_6$-cycloalkyl, —$OCH_2CH_2$—O—$C_1$-$C_4$-alkyl, —$SCF_3$, —$SO_3CF_3$, —$SF_5$, —$CONH_2$, —CONH—$C_1$-$C_4$-alkyl, —CON($C_1$-$C_4$-alkyl)$_2$; $R^1$, $R^2$, $R^4$, and $R^5$ are independently selected from —H, —OH, —O—$C_1$-$C_6$-alkyl, —O—$C_1$-$C_6$-cycloalkyl, halogen, —$NH_2$, —NH—$C_1$-$C_6$-alkyl, —N($C_1$-$C_6$-alkyl)$_2$, —NH—CO—$C_1$-$C_6$-alkyl, —$NHSO_2$—$C_1$-$C_6$-alkyl, —$NHSO_2$N($C_1$-$C_6$-alkyl)$_2$, —NHCONH—$C_1$-$C_6$-alkyl, —NHCON($C_1$-$C_6$-alkyl)$_2$, —NH-aryl; and wherein W is selected from the group consisting of —CH—, —$O^+$—, and —N—; or a pharmaceutically acceptable salt thereof.

In some embodiments, $R^1$, $R^2$, $R^4$, and $R^5$ are —OH, and $R^3$, $R^6$, and $R^8$ are independently selected from the group consisting of —H, —$C_1$-$C_4$ alkyl, —OH, —OMe, and halogen. In a further embodiment, $R^4$ is —OH, while in yet further embodiments $R^1$, $R^2$, and $R^4$ are —OH. In other embodiments of the methods of treatment using the compounds of formula I, W is —$O^+$—. Note that when W is —$O^+$—, the compound will be positively charged, and a counterion such as $Cl^-$ may also be associated with the compound. Examples of specific compounds used in certain embodiments include cyanidin (referred to herein as A18) and delphinidin (referred to herein as A10).

Another aspect of the invention provides a method of treating an IL-17A-mediated disease in a subject, by administering to the subject a therapeutically effective amount of a compound according to formula II:

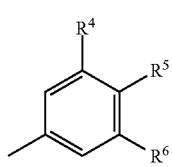

wherein X and Y are independently —CH— or —N—; W is —$CH_2$—, —NH—, or —O—; $R^1$ and $R^2$ are independently —H, —OH, —O—$C_1$-$C_6$-alkyl, —O—$C_1$-$C_6$-cycloalkyl, halogen, —$NH_2$, —NH—$C_1$-$C_6$-alkyl, —N($C_1$-$C_6$-alkyl)$_2$, —NH—CO—$C_1$-$C_6$-alkyl, —$NHSO_2$—$C_1$-$C_6$-alkyl, —$NHSO_2$N($C_1$-$C_6$-alkyl)$_2$, —NHCONH—$C_1$-$C_6$-alkyl, —NHCON($C_1$-$C_6$-alkyl)$_2$, —NH-heteroaryl, —NH-aryl; $R^3$ is selected from —H, —OH, halogen, —$C_1$-$C_6$-alkyl, $C_1$-$C_6$-cycloalkyl, aryl, heteroaryl, —$SO_2$—$C_1$-$C_4$-alkyl, —$SO_2$(NH)—$C_1$-$C_4$-alkyl, —$CF_3$, —O—$C_1$-$C_6$-alkyl, —O—$C_1$-$C_6$-cycloalkyl, —$OCH_2CH_2$—O—$C_1$-$C_4$-alkyl, —$SO_3CF_3$, —$CONH_2$, —CONH—$C_1$-$C_4$-alkyl, —CON($C_1$-$C_4$-alkyl)$_2$; and Ar is an aryl, heteroaryl, bicyclic fused aryl, bicyclic fused heteroaryl group, bicyclic fused cycloalkyl aryl group, bicyclic fused heterocycloalkyl aryl group; or a pharmaceutically acceptable salt thereof.

In some embodiments, Ar is an aryl group according to formula III:

III wherein $R^4$ is —H, —OH, —O—$C_1$-$C_6$-alkyl, —O—$C_1$-$C_6$-cycloalkyl, halogen, —$NH_2$, —NH—$C_1$-$C_6$-alkyl, —N($C_1$-$C_6$-alkyl)$_2$, —NH—CO—$C_1$-$C_6$-alkyl, —$NHSO_2$—$C_1$-$C_6$-alkyl, —$NHSO_2$N($C_1$-$C_6$-alkyl)$_2$, —NHCONH—$C_1$-$C_6$-alkyl, —NHCON($C_1$-$C_6$-alkyl)$_2$, —NH-aryl; and $R^5$ and $R^6$ independently selected from —H, —OH, halogen, —$C_1$-$C_6$-alkyl, $C_1$-$C_6$-cycloalkyl, aryl, heteroaryl, —CN, —SO$_2$—C$_1$-C$_4$-alkyl, —SO$_2$(NH)—C$_1$-C$_4$-alkyl, —CF$_3$, —OCHF$_2$, —OCF$_3$, —O—C$_1$-C$_6$-alkyl, —O—C$_1$-C$_6$-cycloalkyl, —OCH$_2$CH$_2$—O—C$_1$-C$_4$-alkyl, —SCF$_3$, —SO$_3$CF$_3$, —SF$_5$, —CONH$_2$, —CONH—C$_1$-C$_4$-alkyl, —CON(C$_1$-C$_4$-alkyl)$_2$.

In further embodiments, R$^1$, R$^2$, R$^4$, and R$^5$ are —OH, and R$^3$ and R$^6$ are independently selected from the group consisting of —H, —C$_1$-C$_4$ alkyl, —OH, —OMe, and halogen.

In additional embodiments, Ar is a bicyclic fused heteroaryl group or a bicyclic fused heterocycloalkyl aryl group. For example, Ar can be selected from the group consisting of:

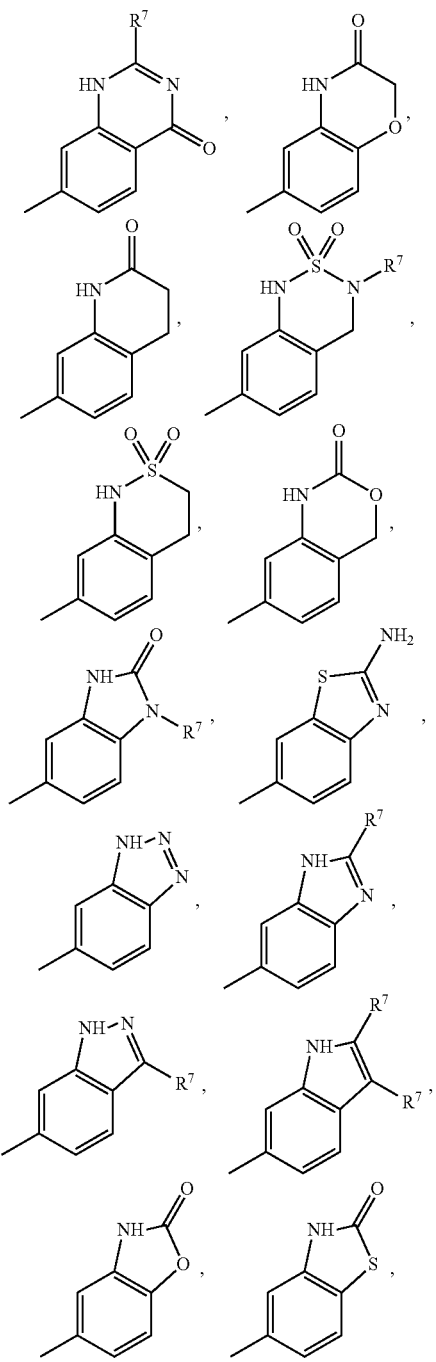

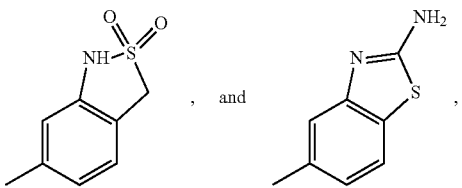

wherein R$^7$ is —H or —C$_1$-C$_6$-alkyl.

In other embodiments of the methods of treatment using the compounds of formula II, R$^4$ is —OH, while in further embodiments, R$^1$, R$^2$, and R$^4$ are —OH. In additional embodiments, W is —O—, while in yet other embodiments X and Y are —CH—. Examples of specific compounds used in certain embodiments of the method of treatment include compounds selected from the group consisting of (−)catechin, (+)catechin, (−)epicatechin, and (+)epicatechin.

Another aspect of the invention provides a method of treating an IL-17A-mediated disease in a subject, by administering to the subject a therapeutically effective amount of a compound according to formula IV or V:

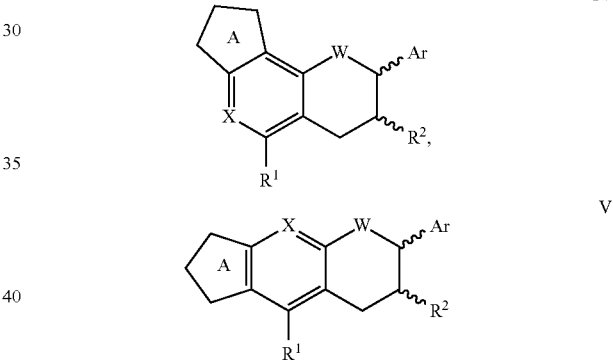

wherein X is —CH— or —N—; W is —CH$_2$—, —NH—, or —O—; Ring A is a heterocyclic 5-membered ring; R$^1$ is selected from —H, —OH, —O—C$_1$-C$_6$-alkyl, —O—C$_1$-C$_6$-cycloalkyl, halogen, —NH$_2$, —NH—C$_1$-C$_6$-alkyl, —N(C$_1$-C$_6$-alkyl)$_2$, —NH—CO—C$_1$-C$_6$-alkyl, —NHSO$_2$—C$_1$-C$_6$-alkyl, —NHSO$_2$N(C$_1$-C$_6$-alkyl)$_2$, —NHCONH—C$_1$-C$_6$-alkyl, —NHCON(C$_1$-C$_6$-alkyl)$_2$, —NH-heteroaryl, —NH-aryl; R$^2$ is selected from —H, —OH, halogen, —C$_1$-C$_6$-alkyl, C$_1$-C$_6$-cycloalkyl, aryl, heteroaryl, —SO$_2$—C$_1$-C$_4$-alkyl, —SO$_2$(NH)—C$_1$-C$_4$-alkyl, —CF$_3$, —O—C$_1$-C$_6$-alkyl, —O—C$_1$-C$_6$-cycloalkyl, —OCH$_2$CH$_2$—O—C$_1$-C$_4$-alkyl, —SO$_3$CF$_3$, —CONH$_2$, —CONH—C$_1$-C$_4$-alkyl, —CONH(C$_1$-C$_4$-alkyl)$_2$; and Ar is an aryl, heteroaryl, bicyclic fused aryl, bicyclic fused heteroaryl group, bicyclic fused cycloalkyl aryl group, bicyclic fused heterocycloalkyl aryl group; or a pharmaceutically acceptable salt thereof.

In some embodiments, Ar is a bicyclic fused heteroaryl group or a bicyclic fused heterocycloalkyl aryl group. For example, Ar can be selected from the group consisting of:

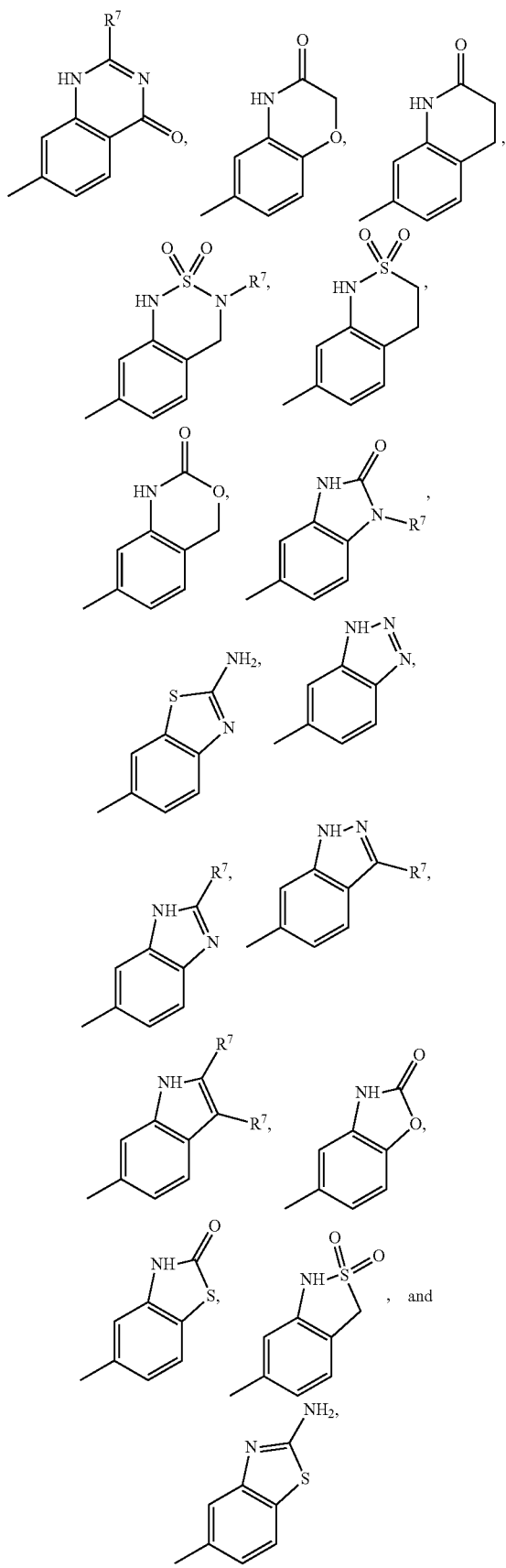

wherein R[7] is —H or —$C_1$-$C_6$-alkyl.

In some embodiments, ring A is selected from the group consisting of:

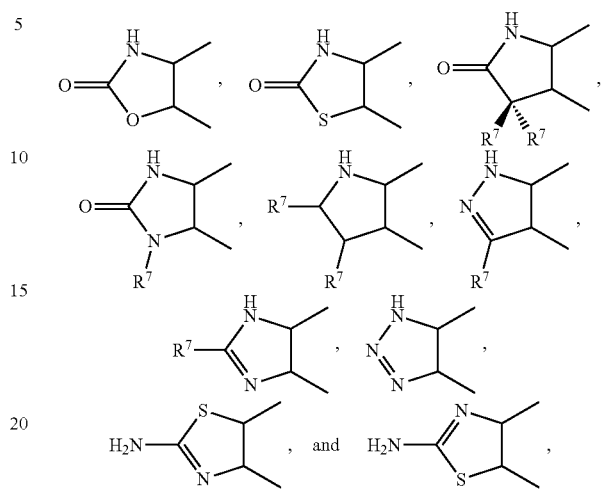

wherein R[7] is —H or —$C_1$-$C_6$-alkyl.

In other embodiments of the method of treatment using a compound according to formula IV or V, R[1] is —OH. In further embodiments, W is —O—, while in other embodiments, X and Y are —CH—.

The compounds of the invention can be used to provide prophylactic and/or therapeutic treatment. The compounds of the invention can, for example, be administered prophylactically to a subject in advance of the occurrence of an interleukin-17A (IL-17A) mediated disease. Prophylactic (i.e., preventive) administration is effective to decrease the likelihood of the subsequent occurrence of IL-17A-mediated disease in the subject, or decrease the severity of IL-17A-mediated disease that subsequently occurs. Prophylactic treatment may be provided to a subject that is at elevated risk of developing IL-17A-mediated disease, such as a subject with a family history of IL-17A-mediated disease. The expression levels and/or activity of IL-17A is a key determinant for cellular sensitivity to the compounds described herein, and thus their levels may be useful as criteria for selecting patients to receive anti-IL-17A-mediated disease therapy using the compounds described herein.

Alternatively, the compounds of the invention can be administered therapeutically to a subject that is already afflicted by IL-17A-mediated disease. In one embodiment of therapeutic administration, administration of the compounds is effective to eliminate the IL-17A-mediated disease; in another embodiment, administration of the compounds is effective to decrease the severity of the IL-17A-mediated disease or lengthen the lifespan of the subject so afflicted. The subject is preferably a mammal, such as a domesticated farm animal (e.g., cow, horse, pig) or pet (e.g., dog, cat). More preferably, the subject is a human.

IL-17A-mediated disease, as defined herein, is a disease in which IL-17A plays a significant role in the pathology of the disease. As further described herein, IL-17A is involved in signaling via the IL-17A receptor complex to transmit signals into cells. The main function of IL-17A is to coordinate local tissue inflammation, which plays a role in a large variety of diseases. Examples of IL-17A-mediated disease include cancer, autoimmune disease, and inflammatory disease.

"Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression. Examples of cancers are sarcoma, breast, lung, brain, bone, liver, kidney, colon, and prostate cancer. In some embodiments, the flavonoid compounds of formulas I—V are used to treat cancer selected from the group consisting of colon cancer, brain cancer, breast cancer, fibrosarcoma, and squamous carcinoma. In some embodiments, the cancer is selected from the group consisting of melanoma, breast cancer, colon cancer, lung cancer, and ovarian cancer. In some embodiments, the cancer being treated is metastatic cancer.

In case of cancer treatment, the method of treating IL-17A-mediated disease can further include the step of ablating the cancer. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, and administration of immunotoxins.

Other examples of IL-17A-mediated diseases include autoimmune diseases and inflammatory diseases. Autoimmune diseases arise from an abnormal immune response of the body against substances and tissues normally present in the body. Examples of autoimmune disease include myocarditis, lupus nephritis, primary biliary cirrhosis, psoriasis, diabetes mellitus type 1, Grave's disease, Celiac disease, Crohn's disease, autoimmune neutropenia, juvenile arthritis, rheumatoid arthritis, fibromyalgia, Guillain-Barré syndrome, multiple sclerosis, and autoimmune retinopathy. For example, some embodiments of the present invention are directed to the treatment of the autoimmune diseases psoriasis or multiple sclerosis.

Inflammatory disease includes a wide variety of disorders characterized by pathological inflammation of tissue. Examples of inflammatory disease include Acne vulgaris, Asthma, Celiac disease, Chronic prostatitis, Glomerulonephritis, Inflammatory bowel diseases, Pelvic inflammatory disease, Reperfusion injury, Rheumatoid arthritis, Sarcoidosis, Vasculitis, house dust mite-induced airway inflammation, and Interstitial cystitis. There is significant overlap between inflammatory disease and autoimmune disease. For example, some embodiments of the present invention are directed to the treatment of the inflammatory disease asthma. The immune system is often involved with inflammatory disorders, demonstrated in both allergic reactions and some myopathies, with many immune system disorders resulting in abnormal inflammation. Accordingly, the IL-17A-mediated diseases also include autoimmune inflammatory disorders.

Candidate agents may be tested in animal models. The animal model should be one appropriate for the IL-17A-mediated disease being treated, such as cancer, an autoimmune disease, or an inflammatory disease. For example, the animal model can be one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof.

Candidate agents can also be evaluated by directly testing their effectiveness as IL-17A inhibitors. For example, an ELISA can be used to characterize IL-17A binding. Suitable methods for characterizing IL-17A inhibiting activity are further described in the examples provided herein.

Administration and Formulation of IL-17A Inhibitors

The present invention also provides pharmaceutical compositions that include flavonoid compounds such as those defined by formulas I-V as an active ingredient, and a pharmaceutically acceptable liquid or solid carrier or carriers, in combination with the active ingredient. Any of the compounds described above as being suitable for the treatment of IL-17A-mediated disease can be included in pharmaceutical compositions of the invention.

The compounds can be administered as pharmaceutically acceptable salts. Pharmaceutically acceptable salt refers to the relatively non-toxic, inorganic and organic acid addition salts of the compounds. These salts can be prepared in situ during the final isolation and purification of the compound, or by separately reacting a purified compound according to formula I with a suitable counterion, depending on the nature of the compound, and isolating the salt thus formed. Representative counterions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005).

The pharmaceutical compositions include one or more compounds according to formulas I through V together with one or more of a variety of physiological acceptable carriers for delivery to a subject, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The compounds of formulas I-V can be administered as a single dose or in multiple doses. Useful dosages of the active agents can be determined by comparing their in vitro activity and their in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, inhaled, rectal, vaginal, topical, nasal, ophthalmic, or parenteral (including subcutaneous, intramuscular, intraperitoneal, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the active compound, or as a solution or suspension in an aqueous liquor or non-aqueous liquid such as a syrup, an elixir, an emulsion, or a draught. Such compositions and preparations typically contain at least about 0.1 wt-% of the active agent. The amount of the compound according to formula I (i.e., active agent) is such that the dosage level will be effective to produce the desired result in the subject.

Inhaled formulations include those designed for administration from an inhaler device. Compositions for inhalation or insufflation include solutions and suspensions in pharmaceutically acceptable, aqueous or organic solvents, or mixtures thereof, aerosols, and powders. Preferably, the compositions are administered by the oral or nasal respiratory route for local or systemic effect. Compositions in preferably pharmaceutically acceptable solvents may be nebulized by use of inert gases. Solution, suspension, or powder compositions may be administered, preferably orally or nasally, from devices that deliver the formulation in an appropriate manner. Nasal spray formulations include purified aqueous solutions of the active agent with preservative agents and isotonic agents. Such formulations are preferably adjusted to a pH and isotonic state compatible with the nasal mucous membranes.

Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Compounds of the invention may be synthesized by synthetic routes that include processes similar to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

Those skilled in the art will appreciate that various synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1

Development of Small Molecule Therapeutics for IL-17A-Mediated Inflammatory Diseases Through computer-aided virtual screening based on the crystal structure of IL-17 RA/IL-17A complex, we have identified two small molecule lead compounds (A18 and A0) that exhibited excellent ability to inhibit IL-17A binding to IL-17RA in in vitro biochemical assay and IL-17A-induced gene expression in cultured cells. A18 (cyanidin) and A0

(catechin) are both flavonoids (polyphenolic compounds), belonging to the family of anthocyanins and flavan-3-ols, respectively. Importantly, A18 showed promising results in preclinical studies for attenuating IL-17A-dependent pathogenesis: attenuation of IL-17-dependent neutrophilia, airway inflammation and airway hyperreactivity, CNS inflammation, skin proliferative response and melanoma cell metastasis. Thus, our small molecule inhibitors (A18, A0 and their analogs) for IL-17A signaling are attractive drug candidates and development of small molecule inhibitors of IL-17A pathway for treatment of inflammatory diseases and cancer is timely and highly significant. In particular, since small molecule inhibitors for IL-17A signaling will address a clear unmet need for severe asthma patients, we expect these future new drugs will have high market attractiveness. Small molecule inhibitors for IL-17A signaling will be equally attractive with great market value for treating other autoimmune diseases and cancer.

Flavonoids are polyphenolic compounds and can be classified into flavanols, flavanones, flavonols, flavones, flavan-3-ols (catechins), anthocyanidins, and isoflavones according to their chemical structures. More than 8,000 different types of flavonoids have been described in nature and are found in most plants including fruits, vegetables, grains, bark, herbs, flowers etc. A18 (cyanidin) is a particular type of anthocyanidin (the sugar-free counterparts of anthocyanins), present as a pigments found in many red berries and other fruits such as apples and plums, with the highest concentrations in the skin of the fruit. A0 (catechin) is a member of flavan-3-ols family, present in white tea, green tea, black tea, grapes, wine, apple juice, cocoa, lentils, and black-eyed peas. Flavonoids and their glycosides have shown a variety of beneficial effects, including anti-atherosclerotic, anti-inflammatory, anti-thrombogenic, anti-tumor, anti-osteoporotic, anti-viral effects in animal and human. Nijveldt et al., Am J Clin Nutr 74, 418-425 (2001).

Most flavonoids administered in preclinical animal experiments and clinical trials have been almost exclusively plant extracts, pure compounds have been utilized in only very few studies. Although antioxidative property of flavonoids has been attributed to their beneficial effects, the precise spectrum of action mechanisms remain poorly understood. Cyanidin (A18) and its glycoside (Cyanidin-3-O-glucoside) are most widely studied flavonoid and have been shown to attenuate development and pathogenesis of asthma, diabetes, atherosclerosis and cancer by providing anti-inflammatory effects. Ding et al., J Biol Chem 281, 17359-17368 (2006); Zhang et al., J Nutr 143, 1248-1253 (2013) Likewise, catechin (A0) and its related compounds have shown widely studied in preclinical and clinical settings, showing efficacy in preventing and/or attenuating inflammatory diseases and cancer. Shay et al., Oxidative medicine and cellular longevity 2015, 181260, (2015). However, despite the overwhelming volume of literature on the beneficial effects of flavonoids for human health, little is known about the molecular mechanisms of action of these compounds.

The current study identifies a novel molecular mechanism for cyanidin, catechin and their related structures based on their ability to inhibit IL-17A-IL-17RA binding, which is supported by computational modeling, in vitro binding measurements, cell-based assay and in vivo studies. This newly identified significant interaction of cyanidin (A18), catechin (A0) and related compounds with the IL-17A receptor explains their anti-inflammatory bioactivities in vivo, since IL-17A is involved in a wide range of chronic inflammatory diseases, including severe asthma, rheumatoid arthritis, multiple sclerosis (MS), psoriasis and cancer.

A challenge of modern medicine has been to develop targeted therapies with high efficacy while minimizing the unnecessary cost. In recent years, there has been an increasing demand for precision medicine: use of molecular profiling to better understand the genetic makeup and molecular basis of a specific disease in patients. The benefits of applying molecular profiling to drug discovery and development include: decreased failure rates at all stages of the drug development pipeline; faster progression from discovery through to clinical trials; and more successful therapies for patient subgroups. Since we have clearly defined IL-17A-IL-17RA as the molecular target of A18- and A0-derived drugs, A18- and A0-derived drugs can be developed to specifically target the patient populations with IL-17A-dependent diseases. We anticipate that autoimmune and/or cancer patients with increased Th17-IL-17A signature profiles will have a better responding rate to A18- and A0-derived drugs. Considering the large scales of ongoing clinical trials on anti-IL-17A antibody (Cosentyx/secukinumab from Novartis), IL-17A-specific biomarkers is being actively developed. Thus, A18- and A0-derived drugs have the potential to provide a new generation small molecule drugs for personalized medicine to treat IL-17A-dependent autoimmune and cancer patients.

Methods

Reagents, cell culture and mice. Purified proteins of human IL-17A, human IL-17E (IL-25), human IL-17RA-Fc (extracellular domain 1-322 AA fused with Fc region of human IgG1 at the C-terminus), human IL-17RB-Fc (extracellular domain 1-289 AA fused with Fc region of human IgG1 at the C-terminus), human horseradish peroxidase (HRP)-conjugated IgG Fc secondary antibody were purchased from Sino Biological Inc. Human and mouse IL-17A and mouse IL-23 used for cell culture and animal injection were purchased from R&D Systems. Human mammary epithelial cells were maintained in Medium 171 plus mammary epithelial growth supplement (MEGS) purchased from Invitrogen, which contain bovine pituitary extract (BPE) (0.4% v/v), recombinant human insulin-like growth factor-I (1 µg/ml), hydrocortisone (0.5 µg/ml) and human epidermal growth factor (3 ng/ml). A549 cells were maintained in RPMI supplemented with 10% FCS and 100 U/ml penicillin and 100 µg/ml streptomycin. All mice were obtained from Jackson laboratory.

High Throughput virtual screening. Virtual screening was performed using Maestro 9.6 software (Schrödinger Release 2013-3, Schrödinger, LLC, New York, N.Y., 2013.) and High Performance Computing (HPC) cluster server at Case Western Reserve University with the following procedures: 1) Ligand preparation. The compound library for screening which contains 89,253 compounds in SDF format was downloaded from the online sources of NCI Plated 2007 and NCI Diversity 3. Before docking, all compounds were pre-processed using 'LigPrep' module in Maestro. Each compound was desalted and of which possible ionization states at the pH range of 5.0-9.0 and tautomers were generated by Epik mode in the force field of OPLS_2005. 2) Protein preparation. The structure of Interleukin-17 receptor A (IL-17RA) was derived from the Protein Data Bank (PDB code: 4HSA or 3JVF). Before docking, the protein was processed and refined with 'Protein Preparation' module in Maestro. In general, hydrogen atoms were added, water molecules were removed, H-bond assignment was optimized, and restrained minimization was conducted using the force field of OPLS_2005. 3) Docking grid generation. The segment (residues 36-47) derived from Interleukin-17A (IL-17A) or Interleukin-17F (IL-17F) which forms complex with IL-17RA was used to define the center of docking pocket, the scaling factor and the partial charge cutoff of the van der Waals (VDW) radii were set to 1.0 and 0.25 respectively. This step was performed using 'Receptor Grid Generation' module in Maestro. 4) Glide docking. Initially, all of the prepared compounds were docked into the defined binding pocket of IL17-RA using the HTVS (high throughput virtual screening) mode and ranked by the docking score. The two sets of the top 2500 compounds (from 4HSA and 3JVF respectively) were then both re-docked into IL17-RA separately using SP (standard-precision) and XP (extra-precision) mode respectively. The compounds seen in both sets were selected and compared for their SP and XP docking scores, and their docking conformations were then carefully inspected by visual observation. Eventually, 64 potential compounds were purchased for bioassay. The docking simulations were conducted on High Performance Computing (HPC) cluster server at Case Western Reserve University and the docking conformation analysis was performed using PyMol.

IL-17A-IL-17RA binding assay. ELISA plates were coated with human IL-17A or IL-17E (2 μg/ml in PBS). Human IL-17RA-Fc or human IL-17RB-Fc (150 ng/ml) were added and incubated for 1 h, followed by incubation with human HRP-conjugated anti human IgG Fc secondary antibody for 1 h. ELISA were finally developed using tetramethylbenzidine substrate.

Surface plasmon resonance (SPR). Binding of A18 to IL-17RA was conducted on Biacore T100 instrument. Purified IL-17RA was immobilized on CM5 sensor chip using amine coupling kit (GE healthcare). A18 of different concentrations were flown over the chip in PBSPP+ buffer (20 mM Phosphate, 2.7 mM KCl, 137 mM NaCl and 0.05% P20, pH 7.4). The chip was regenerated with 2M GnHCl. Binding KD was determined by Biaevaluation software.

Fluorescence binding measurement. The recombinant human IL-17RA ectodomain was expressed in baculovirus-infected Sf-9 cells and purified as described previously. Liu et al., Nat Commun 4, 1888 (2013). The compound A18 or A0 was obtained from NCI. The purified IL-17RA protein (final concentration at 1 uM) was mixed with various concentrations of compound A0 in the solution consisting of 20 mM Tris, pH 7.5, 150 mM NaCl, and 5% DMSO in a 96-well black flat-bottom microplate (Greiner Bio-One). The reaction mixtures were incubated at room temperature at 120 rpm for 10 min, and fluorescence intensity was measured on a 2300 EnSpire Multimode Plate Reader (PerkinElmer) with excitation (265 nm) and emission (336 nm) wavelengths for A18 or with excitation (240 nm) and emission (337 nm) wavelengths for A0. The fluorescence signal (relative fluorescence intensity) was obtained by subtracting the background fluorescence of buffer and compound A0, and plotted as a function of the concentration of compound A0. The fluorescence quenching was observed as a consequence of the protein-ligand interaction at dose-dependent concentrations of compound A0, and the binding constant of compound A0 to IL-17RA was estimated by one-site total binding fit model (GraphPad Prism).

Peritoneal administration of IL-17A. Eight-week WT BALB/cJ female mice were subjected to intraperitoneal injection (i.p.) of PBS, 1 μg of IL-17A with or without A18 (30 μg per mouse). The peritoneal cavity was lavaged with 5 ml ice-cold PBS at 6 h post treatment. Peritoneal cells were counted and quantified by differential cell counting.

Intranasal injection of IL-17A. Eight-week WT BALB/cJ female mice were subjected to intranasal injection of PBS, 1 μg of IL-17A with or without A18 (4 μg per mouse). Lung tissue was collected by PBS at 6 h post treatment.

Intradermal injection of IL-17A. The ears of 8-week WT C57BL/6 female mice were injected intradermally with 20 μl PBS, either alone or containing 500 ng recombinant mouse IL-17A with or without A18 (30 μg per mouse). After 7 days after injection, the mice ears were fixed in 10% formalin in PBS and stained with hematoxylin and eosin (H&E). Epidermal thickness was quantified by Image J.

Adoptive transfer of EAE by Th17. To prepare MOG-specific polarized Th17 cell populations, drain lymph node cells were prepared from 10-week WT C57BL/6 female mice immunized with MOG 35-55 at day 10 postimmunization. Cells were cultured for 5 days with MOG 35-55 at a concentration of 25 mg/ml under Th17 cell (20 ng/ml IL-23) polarizing condition. For induction of Th17-mediated EAE, 10-week WT C57BL/6J female mice were injected i.p. with $3.0 \times 10^7$ polarized MOG 35-55-specific Th17 cells/mouse with or without A18 (30 μg per mouse) 4 h after 500 Rad sublethal irradiation. A18 (30 μg per mouse) was continuously administered i.p. to the treated mice every other day after Th17 injection. At the peak of disease, the mice were sacrificed and perfused with PBS. The spinal cords were fixed in 10% formalin for staining with H&E. The Brains were removed for isolation of infiltrating cells.

Isolation and analysis of inflammatory cells from brain. Brains were homogenized in ice-cold tissue grinders and filtered through a 100 mm cell strainer, and the cells were collected by centrifugation at 400 g for 5 min at 4° C. Cells were resuspended in 10 ml of 30% Percoll (Amersham Bioscience) and centrifuge onto a 70% Percoll cushion in 15 ml tubes at 800 g for 30 min. Cells at the 30%-70% interface were collected and were subjected to flow cytometry. Fluorescence-conjugated CD4, CD8, CD45, Ly6G1 antibodies and isotype controls were purchased from BD Biosciences. F4/80 was obtained from Serotech.

High-fat-diet intervention. Starting at 4 weeks of age, WT C57BL/6 male mice were fed with 10 kcal % fat chow diet (CD) or a 60 kcal % HFD for 14 weeks. HFD+A18 group of mice were i.p. injected with A18 (30 μg per mouse) daily for 10 days before subjection to AHR measurement. Both CD (D12450B) or HFD (D12492) were obtained from Research Diets, Inc.

Measurement of AHR. AHR was measured in mice in response to increasing doses of inhaled methacholine. Mice were anesthetized with i.p. pentobarbital sodium (60 mg/kg). After the intubation and the placement of a 19-gauge cannula through a tracheotomy incision, the cannula was affixed with a silk suture ligation. Mice were connected to a computer-controlled piston ventilator run at a rate of 150 breaths/min, a tidal volume of 0.2 ml, and a positive end-expiratory pressure of 2-3 cm $H_2O$ (Flexivent). Mice were then administered a muscle relaxant (pancuronium bromide, 800 mg/kg), and the lungs were expanded twice to total lung capacity at an amplitude pressure of 30 cm $H_2O$. Each mouse was aerosolized with methacholine in saline at doses of 0 mg/ml, 12.5 mg/ml, 25 mg/ml, and 50 mg/ml, delivered over 10 s through an in-line nebulizer. Lung resistance ($R_L$) was obtained through forced oscillation technique by FlexiVent 5.2 (Flexivent; Scireq) software.

House dust mite (HDM)-induced asthma. WT C57BL/6 mice were sensitized intratracheally (i.t.) with HDM (*Dermatophagoides farina*, 100 μg per mouse, Greer Laboratories) on day 0 and subsequently challenged (i.t.) with HDM (100 μg per mouse) from day 7 for 5 days. AHR measurement and tissue collection were performed after 72 h of last HDM challenge. HDM+A18 group of mice were i.p. injected with A18 (30 µg per mouse) daily for the whole experimental period.

ELISA. Groα and IL-17A levels were assayed by ELISA kits (R&D systems) according to the manufacturer's instruction.

Real-time PCR. Total RNA was extracted from spinal cords and cultured astrocytes with TRIzol (Invitrogen) according to the manufacturer's instructions. All gene expression results are expressed as arbitrary units relative to expression of the gene encoding beta-actin.

Statistical analysis. All values were determined by Student's t tests. Unless otherwise specified, all results are shown as mean and the standard error of the mean (mean±SEM). A p value of <0.05 was considered significant.

Results

Figure 1:
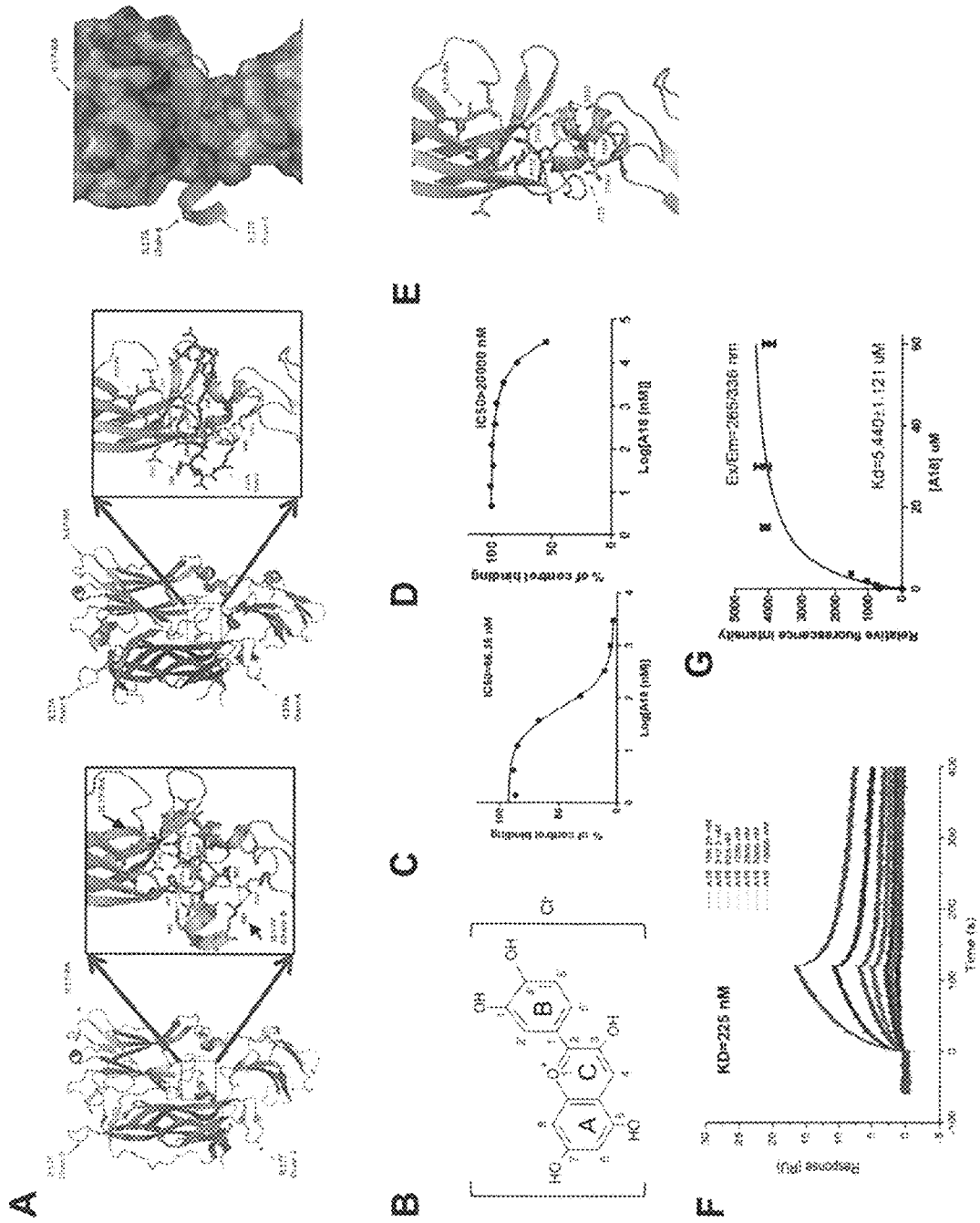
FIG. 1 (A-G) illustrates Identification of A18 as lead small molecule inhibitor for IL-17A binding to IL-17RA. A. Crystal structures of IL-17F-IL-17RA complex (PDB code: 3JVF) and IL-17A-IL-17RA complex (PDB code: 4HSA). Several prominent amino acid residuals of IL-17RA make a deep pocket structure for interaction with contacting amino acid residuals of IL-17F or IL-17A. This pocket structure of IL-17RA binding interface was used for docking platform for screening small molecule inhibitors. B. Chemical structure of A18. The CAS name of A18 is 2-(3,4-Dihydroxyphenyl)-3,5,7-trihydroxy-1-benzopyrylium chloride. The core of A18 (cyanidin) contains one heterocyclic benzopyran ring (as the C ring), one fused aromatic ring (as the A ring) and one phenyl constituent (as the B ring). In the cation form, anthocyanidins have two double bonds in the C ring and hence carry a positive charge. C-D. Purified IL-17A or IL-17E proteins (2 µg/ml) were coated onto 96-well plate, and IL-17RA-Fc or IL-17RB-Fc proteins (150 ng/ml) were added with serial dilutions of A18. The bound IL-17RA-Fc was detected by a HRP-conjugated anti-Fc antibody. A18 showed great inhibition efficacy for IL-17-IL-17RA binding (C), but not for IL-17E-IL-17RB binding (D). E. Docking A18 to human IL-17RA binding pocket. *dash lines stand for potential hydrogen bonds formed between A18 and critical amino acid residues in the docking pocket of IL-17RA. F. Surface plasmon resonance (SPR) analysis of A18 binding to IL-17RA. Binding of A18 to IL-17RA was conducted on Biacore T100 instrument. A18 (156.25 nM to 10000 nM) was injected over the IL-17RA-immobilized surface (on CM5 sensor chip). The binding KD was determined by Biaevaluation software and expressed as resonance units (RU). G. The purified IL-17RA protein (at final concentration of 1 uM) was mixed with various concentrations of compound A18 in the solution consisting of 20 mM Tris, pH 7.5, 150 mM NaCl, and 5% DMSO in a 96-well black flat-bottom microplate. The fluorescence intensity was measured on a 2300 EnSpire Multimode Plate Reader (PerkinElmer) with excitation (265 nm) and emission (336 nm) wavelengths. The fluorescence signal (relative fluorescence intensity) was corrected by background subtraction and plotted as a function of the concentration of compound A18. The binding constant of compound A18 to IL-17RA was estimated by one site binding (hyperbola) fit model (GraphPad Prism).

Structure-based screening of small molecule inhibitors for IL-17-IL-17RA binding. The crystal structure of the human IL-17RA extracellular domain complexed to an IL-17F or IL-17A homodimer has been resolved. Liu et al., Nat Commun 4, 1888 (2013); Ely et al., Nat Immunol 10, 1245-1251 (2009). Both IL-17F and IL-17A interact with IL-17RA in a very similar manner and the interaction interface is highly conserved (FIG. 1A). The manner of complex formation is unique for cytokines, and involves two fibronectin-type III domains (D1 and D2) of IL-17RA engaging IL-17 within a groove between the IL-17 homodimer interface in a knob-and-hole fashion. This 'partial' signaling complex implicates the presence of biologically relevant forms of the IL-17RA-IL-17F and IL-17RA-IL-17A complexes. IL-17RA forms an extensive binding interface with IL-17A, mainly mediated by IL-17RA D1 domain. There are three major interaction sites at the binding interface, among which the second site (FIG. 1A) is the most prominent one, composed of the IL-17RA D1 C'C loop (L86-R93) which slots into a deep binding-pocket flanked by the N-terminal extension and strand 2 of IL-17F/A chain B and strand 3 of IL-17F/A chain A. Several critical amino acid residues (N89, D121, Q124, D262) adjacent to D1 C'C loop on IL-17RA, form a deep pocket for interaction with IL-17F/A chain B.

Based on the structural information of IL-17RA, we performed computer-aided docking-based virtual screening for small molecule inhibitors that disrupt IL-17A-IL-17RA interaction using the pocket structure defined in the black box in FIG. 1A. The segment (residues 35-46) derived from Interleukin-17A (IL-17A) or residues 36-47 derived from Interleukin-17F (IL-17F) which forms complex with IL-17RA was used to define the center of docking pocket. The public compound database (NCI Plated 2007 and NCI Diversity 3) containing ~0.1 million compounds were virtually screened. Among top hit list, two promising candidates (A18 and A0) (FIG. 1E and FIG. 2A) exhibited excellent inhibition efficacy for IL-17A-IL-17RA binding and binding behavior to IL-17RA (FIGS. 1C-G and FIGS. 2C-D).

The CAS (Chemical Abstracts Service) name of A18 is 2-(3,4-Dihydroxyphenyl)-3,5,7-trihydroxy-1-benzopyrylium chloride. The core of A18 (also called cyanidin, a particular form of anthocyanidins) has the typical C6-C3-C6 flavonoid skeleton, which contains one heterocyclic benzopyran ring (as the C ring), one fused aromatic ring (as the A ring) and one phenyl constituent (as the B ring). In the cation form, anthocyanidins have two double bonds in the C ring and hence carry a positive charge. To test the ability of A18 to disrupt the IL-17A-IL-17RA binding, purified IL-17A or IL-17E (as a control) were coated onto 96-well plates, followed by the addition of IL-17RA-Fc or IL-17RB-Fc with serial dilutions of A18. The bound IL-17RA-Fc was detected by a HRP-conjugated anti-Fc antibody. A18 showed excellent inhibition efficacy for IL-17A-IL-17RA binding (FIG. 1C) but not for IL-17E-IL-17RB binding (FIG. 1D). Consistently, FIG. 1E shows that A18 fits nicely into the IL-17 binding pocket with all the hydroxyl groups of A18 forming H-bonds with critical amino acid residues in IL-17RA especially involving D121, P122, S167, S168, and D262. The A18 binding site partially overlaps with that for IL-17A (FIG. 1A), thus providing a structural basis for the A18 inhibition on IL-17A-IL-17RA binding. Complementary to IC50, the binding affinity KD of the compound/IL-17RA complex is also a good indication of the compound property. We have used SPR (Surface Plasmon Resonance—Biacore) technology to measure the affinity using purified the extracellular domain (ECD) of human IL-17RA (FIG. 1F). A18 can directly bind IL-17RA ECD with a KD of 225 nM. Consistently, a fluorescence-based method also independently showed the potent binding with the KD~5 µM (FIG. 1G). Note that the affinity variations by two different methods are due to the experimental conditions with the former having IL-17RA immobilized and the latter having IL-17RA diffused in solution. The SPR method may better mimic the cellular condition where IL-17RA is immobilized onto the membrane.

Figure 2:
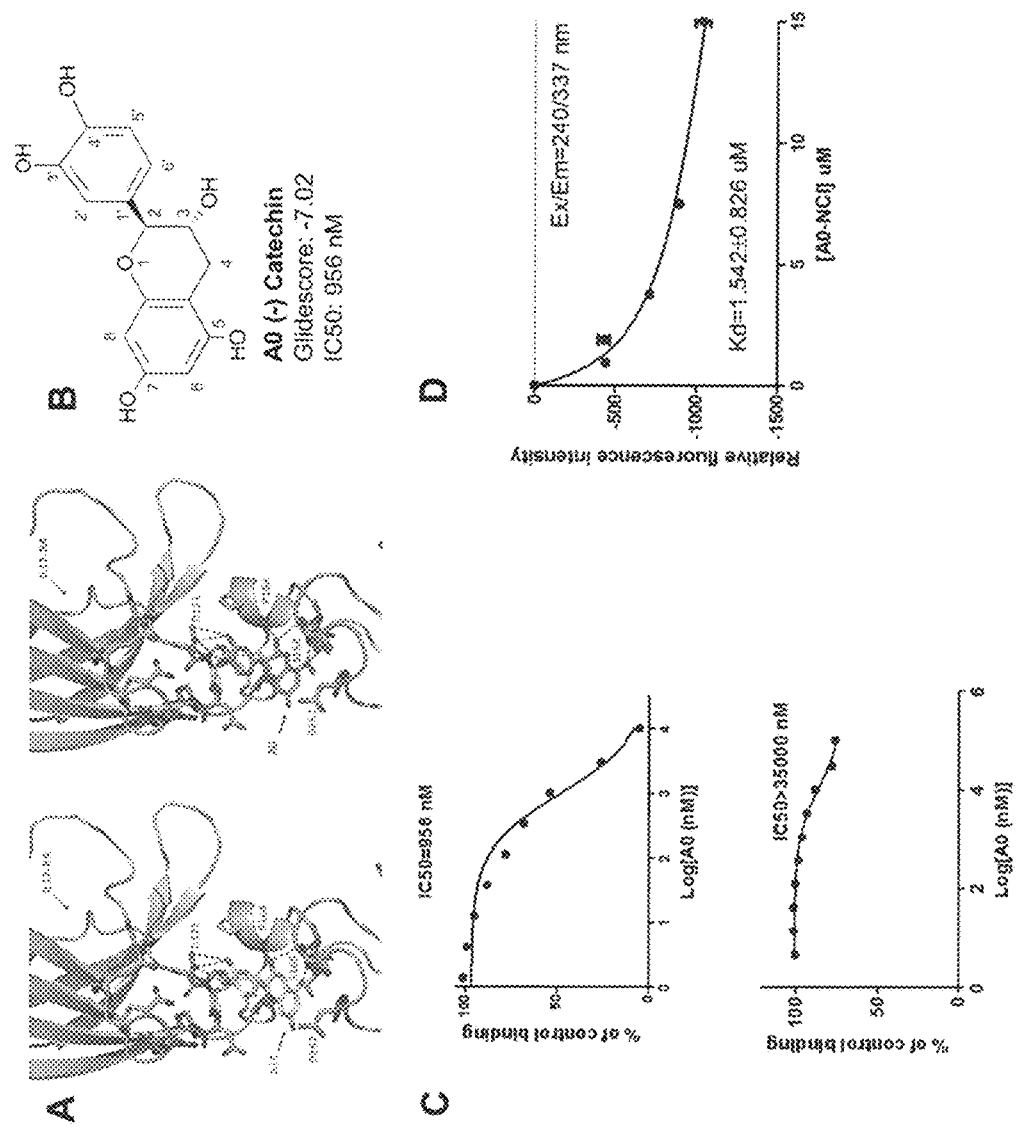
FIG. 2 (A-D) provides graphs and images showing the identification of A0 as lead small molecule inhibitor for IL-17A binding to IL-17RA. A. Comparison of docking of A18 and A0 to IL-17RA binding pocket. *Red dash lines stand for potential hydrogen bonds formed between A18 or A0 and critical amino acid residues in the docking pocket of IL-17RA. B. Chemical structure of A0. The IUPAC name of A0 is (2S,3R)-2-(3,4-dihydroxyphenyl)-3,4-dihydro-2H-chromene-3,5,7-triol. Similar to A18, A0 possesses two benzene rings (A- and B-rings) but a different dihydropyran heterocycle (the C-ring) and is thus not positively charged. C-D. Purified IL-17A or IL-17E proteins (2 µg/ml) were coated onto 96-well plate, and IL-17RA-Fc or IL-17RB-Fc proteins (150 ng/ml) were added with serial dilutions of A18. The bound IL-17RA-Fc was detected by a HRP-conjugated anti-Fc antibody. A0 showed great inhibition efficacy for IL-17-IL-17RA binding (C), but not for IL-17E-IL-17RB binding (D). E. Docking A18 to IL-17RA binding pocket. *dash lines stand for potential hydrogen bonds formed between A18 and critical amino acid residues in the docking pocket of IL-17RA. F. The recombinant human IL-17RA ectodomain (final concentration at 1 uM) was mixed with various concentrations of compound A0 in the solution consisting of 20 mM Tris, pH 7.5, 150 mM NaCl, and 5% DMSO). The reaction mixtures were incubated at room temperature for 10 min, and fluorescence intensity was measured on a 2300 EnSpire Multimode Plate Reader (PerkinElmer). The fluorescence signal (relative fluorescence intensity) was obtained by subtracting the background fluorescence of buffer and compound A0, and plotted as a function of the concentration of compound A0. The fluorescence quenching was observed as a consequence of the protein-ligand interaction at dose-dependent concentrations of compound A0, and the binding constant of compound A0 to IL-17RA was estimated by one-site total binding fit model (GraphPad Prism).

The CAS (Chemical Abstracts Service) name of A0 is 2-(3,4-dihydroxyphenyl)-3,4-dihydro-2H-chromene-3,5,7-triol. The core of A0 (also called Catechin) possesses two benzene rings (called the A- and B-rings) and a dihydropyran heterocycle (the C-ring) with a hydroxyl group on carbon 3. The A ring is similar to a resorcinol moiety while the B ring is similar to a catechol moiety. There are two chiral centers on the molecule on carbons 2 and 3. Therefore, it has four diastereoisomers. Two of the isomers are in trans configuration and are called catechin and the other two are in cis configuration and are called epicatechin. To test the ability of A0 to disrupt the IL-17A-IL-17RA binding, purified IL-17A or IL-17E (as a control) were coated onto 96-well plates, followed by the addition of IL-17RA-Fc or IL-17RB-Fc with serial dilutions of A18. The bound IL-17RA-Fc was detected by a HRP-conjugated anti-Fc antibody. A0 showed excellent inhibition efficacy for IL-17A-IL-17RA binding but not for IL-17E-IL-17RB binding (FIG. 2C). Consistently, FIG. 2A shows that A0 fits nicely into the IL-17A binding pocket with all the hydroxyl groups of A0 forming H-bonds with critical amino acid residues in IL-17RA especially involving D121, P122, S167, S168, and D262, which is very similar to how A18 docks to IL-17RA. We have used fluorescence binding essay to measure the direct binding of A0 with purified ECD of IL-17RA. The fluorescence quenching was observed as a consequence of the protein-ligand interaction at dose-dependent concentrations of compound A0, and the binding constant of compound A0 to IL-17RA was estimated by one-site total binding fit model (GraphPad Prism) (FIG. 2D), which is in the same range as A18 (FIG. 1G).

We note that in our top 64 compound list, A10 (FIG. 8D) is also similar to A18 in the chemical structure and docks similarly to A18/A0. Indeed, FIG. 8D shows that A10 can potently inhibit the IL-17A binding to IL-17RA. Thus we have identified three promising lead compounds (A18, A10, A0) that may act as inhibitors of IL17A-mediated signaling.

Figure 3:
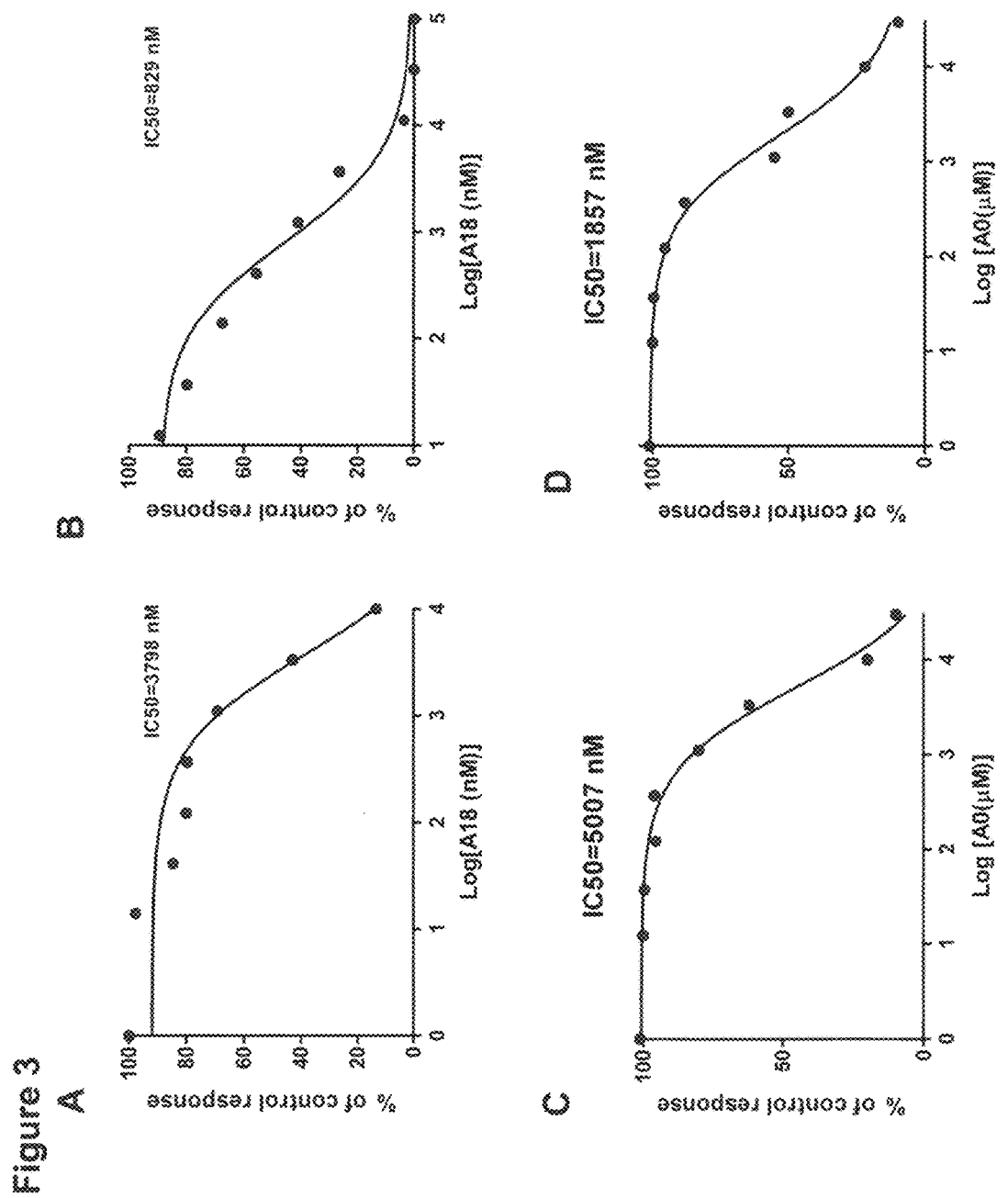
FIG. 3 (A-D) provides graphs showing A18 and A0 inhibited IL-17-induced CXCL (Groα) chemokine production in both human mammary epithelial cells and A549 cells. Human mammary epithelial cells (A and C) and A549 cells (B and D) were treated with IL-17 (100 ng/ml) in the present of different concentrations of A18 or A0 for 24 h. Groα production in the culture supernatant was measured by ELISA.

A18 and A0 inhibited IL-17A-induced chemokine gene expression in cultured cells. Since A18 and A0 were able to block IL-17A-IL-17RA interaction in biochemical assay using purified proteins, we further investigated whether A18 and A0 exhibit inhibitory effect on IL-17A bioactivity in a cell-based assay. Human CXCL1 (Groα) is a well-known IL-17A target gene. Witowski et al., J Immunol 165, 5814-5821 (2000). We measured IL-17A-induced CXCL1 production in the presence of increasing doses of A18 or A0 in two IL-17A responsive cell lines-human mammary epithelial cells (HMEC) and A549 cells. As shown in FIG. 3, A18 and A0 greatly inhibited IL-17A-mediated CXCL1 production in both cell lines. This result suggested A18 and A0 were indeed able to inhibit IL-17A bioactivity in a dose-dependent manner in cultured cells. Furthermore, although IL-17F is much weaker ligand for induction of cytokines, A18 and A0 were able to block IL-17F-induced gene expression in the indicated epithelial cells (data not shown).

Figure 4:
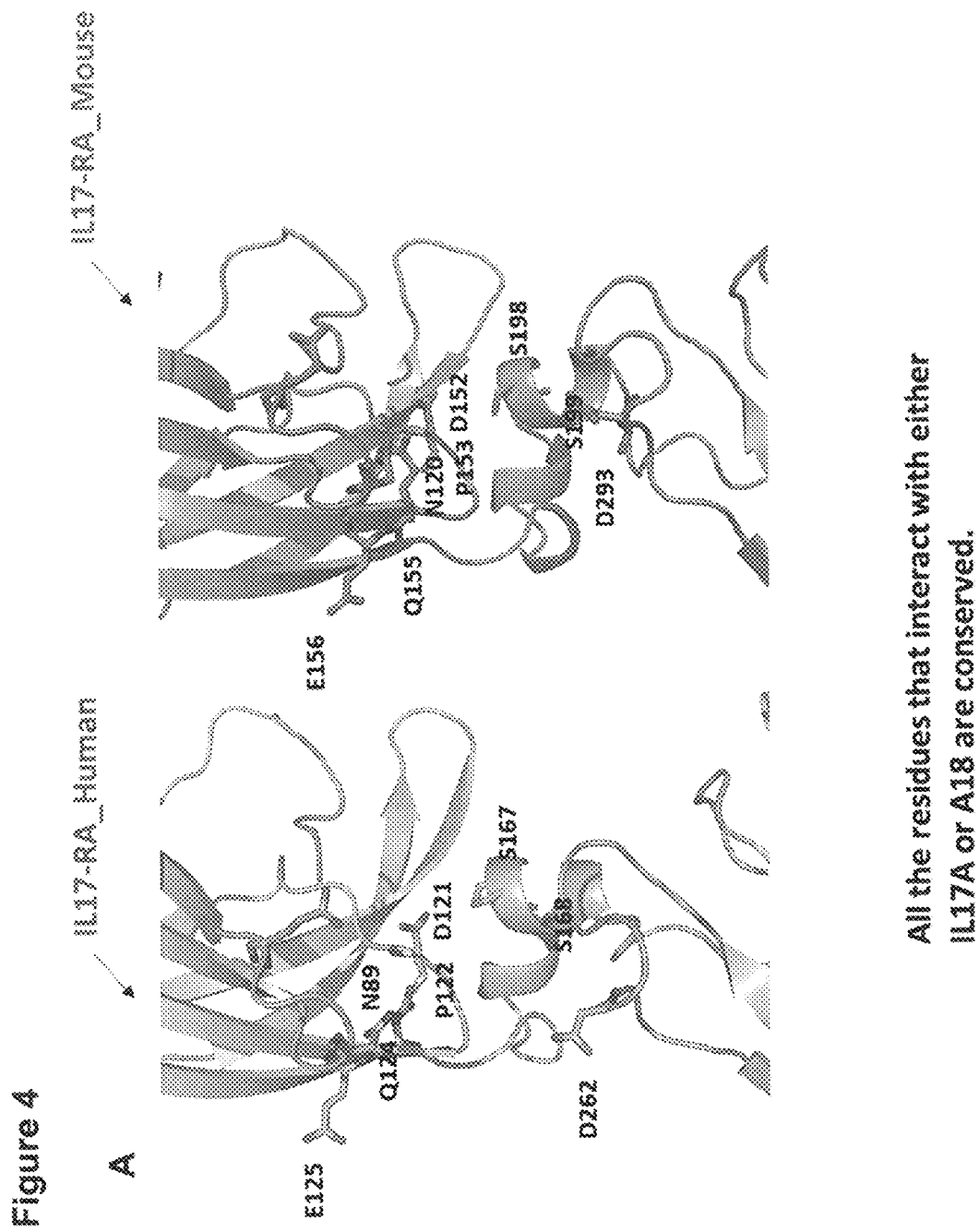
FIG. 4 (A-C) provides graphs and images showing A18 inhibited IL-17-induced peritoneal neutrophilia and lung inflammation in mice. A. Comparison of docking A18 to human and mouse IL-17RA binding pockets. The critical amino acid residues in the docking pockets of both human and mouse IL-17RA are conserved *dash lines stand for potential hydrogen bonds formed between A18 and RA. B. IL-17A (1 µg per mouse) with or without A18 (30 µg per mouse) was administered by i.p. injection into 8-week WT BALB/cJ female mice. After 6 h, peritoneal lavage was collected and cellular infiltration was quantified by differential cell counting. Graph represents percentages of neutrophils in peritoneal lavages from mice. Error bar, SEM; n=5 per group. *P<0.05. Arrows indicate neutrophils. C. IL-17A (1 µg per mouse) in 20 µl of PBS with or without A18 (4 µg per mouse) was administered by intranasal injection into 8-week WT BALB/cJ female mice. The graph show real-time PCR analysis of gene expression in lung tissue after 4 h injection. Error bar, SEM; n=5 per group.
Figure 4:
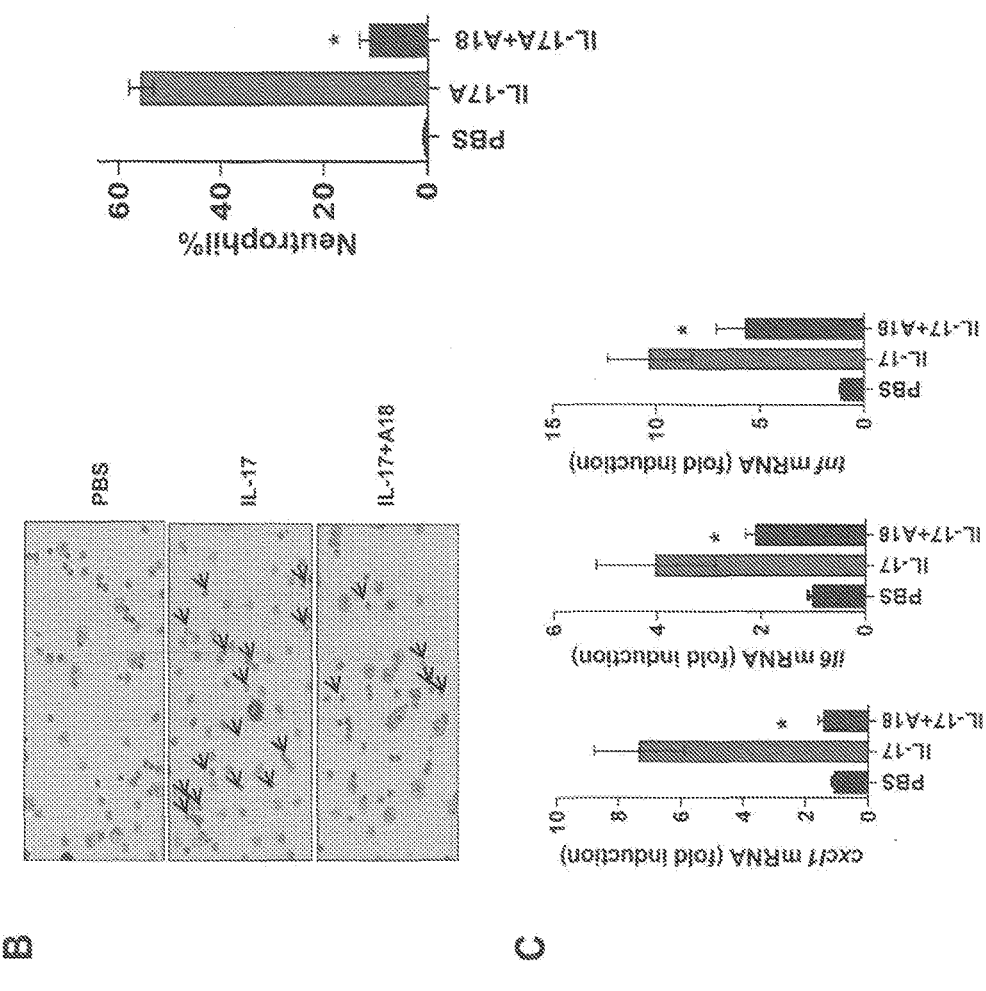

A18 inhibited IL-17A-induced intraperineal neutrophilia and lung inflammation. After we have clearly showed that A18 inhibited IL-17A binding to IL-17RA with purified proteins and IL-17A bioactivity in cultured cells, we then investigated whether A18 can inhibit IL-17A-mediated bioactivity in vivo. It is important to note that sequence alignment and modeling showed that mouse IL-17RA share sequence similarity to human and particularly all the residues in the docking pocket that interact with either IL-17A or A18 are conserved (FIG. 4A). IL-17A has been shown to induce neutrophil infiltration to the peritoneum, mainly due to induction of neutrophil-chemoattractant chemokines including CXCL1. Gonzalez-Garcia et al., J Immunol 182, 2665-2671 (2009); Harrington et al., Nat Immunol 6, 1123-1132 (2005). IL-17A (1 µg per mouse) with or without A18 (30 µg per mouse) was administered by intraperitoneal injection into 8-week BALB/c mice female mice. After 6 h, peritoneal lavage was collected and cellular infiltration was quantified by differential cell counting. While IL-17A indeed induced intraperineal neutrophilia, A18, co-injected with IL-17A, greatly attenuated IL-17A-induced intraperineal neutrophilia (FIG. 4B). Previously, we have shown that intranasal injection induced airway inflammation as indicated by upregulation of proinflammatory genes. Swaidani et al., J Immunol 182, 1631-1640 (2009). We injected IL-17A (1 µg per mouse) with or without A18 (4 µg per mouse) intranasally into WT BALB/c mice female mice for 4 h. A18 greatly inhibited IL-17A-induced gene expression (FIG. 4C). These results suggest that A18 is able to inhibit IL-17A bioactivity in these proof-of-concept animal studies.

A18 attenuated airway hyperreactivity (AHR) in mouse model of severe asthma. Asthma has become an epidemic affecting 300 million people in the world including ~25 million people in the United States. Airway inflammation, smooth muscle bronchoconstriction leading to airflow obstruction, and mucous hypersecretion are clinical hallmarks of asthma. Asthma is well-known as the result of sensitization to a variety of environmental allergens (atopic asthma). Patients with mild to moderate asthma typically have disease characterized by Th2 cytokine expression with eosinophilic inflammation and respond well to inhaled corticosteroids (ICS), but some eventually develop refractory disease. Those with more severe, steroid-resistant disease appear to have neutrophilic airway inflammation with less reversible airflow obstruction. Th17 cells and associated cytokine IL-17A have been noted to play a significant role in neutrophil-predominant disease. Chesne et al., American journal of respiratory and critical care medicine 190, 1094-1101 (2014). Accumulating evidence suggests that aberrant IL-17A production is a key determinant of severe and steroid-resistant forms of asthma. Silverpil, E. & Linden, A., Expert review of respiratory medicine 6, 173-186 (2012). A pre-specified subset analysis suggested that patients with "high-reversibility" asthma might benefit from anti-IL-17A therapy. Busse et al., American journal of respiratory and critical care medicine 188, 1294-1302 (2013). Notably, both allergens (such as fungal sensitization) and environmental factors (e.g. cigarette smoking) can exacerbate asthma. In addition, recent studies have shown that obesity is a major risk factor for the development of asthma and contributes to asthma severity. Obese individuals with asthma respond poorly to typical asthma medications (including corticosteroids). A recent study indicates that IL-17A signaling provides a critical link between obesity and asthma. Kim et al., Nature medicine 20, 54-61 (2014). Therefore, the IL-17A pathway is an important target for the treatment of severe and steroid-resistant asthma.

Emerging evidences confirm the association between obesity and asthma (especially nonatopic asthma). Paggiaro et al., Annals of allergy, asthma & immunology: official publication of the American College of Allergy, Asthma, & Immunology 108, 217-218 (2012). Mice fed with high fat diet (HFD) developed airway hyperreactivity (AHR) that is dependent on IL-17A. Since HFD-induced AHR is a proven IL-17A-mediated disease model, we investigated whether A18 could attenuate this airway disease. Wild-type C57Bl/6 male mice were fed with chow diet (CD) or high fat diet (HFD) for 14 weeks starting at 4-weeks of age. A18 (30 µg per mouse) was i.p injected into the mice on HFD for the last 10 days of HFD feeding (HDFA18 group). Consistent with the previous report (Kim et al., Nat Med 20, 54-61 (2014)), HFD-fed mice (with or without A18 treatment) had increased IL-17A production in cultured lung cells compared to that of CD-fed mice, indicating that A18 had no impact on HFD-induced the production of IL-17A in the lung. Importantly, A18 treatment substantially attenuated HFD-induced AHR and inflammatory gene expression (FIG. 5A-B), implying the potential therapeutic role of A18 in treatment of IL-17A-dependent asthma, including obesity-associated severe asthma.

Figure 5:
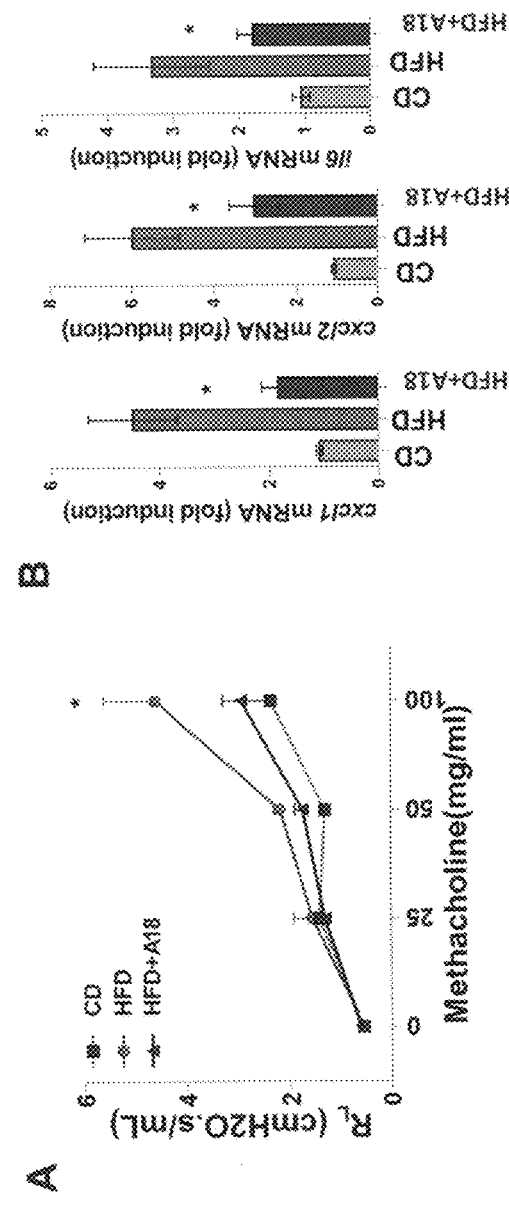
FIG. 5 (A-D) provides graphs showing A18 attenuated HFD-induced airway hyperreactivity (AHR) and HDM-induced allergic airway inflammation. A-B. WT C57BL/6J male mice were fed with CD or HFD for 14 weeks starting at 4-weeks of age. A18 (30 µg per mouse) was i.p injected into mice for the last 10 days of HFD feeding (HDF+A18 group). A. Lung resistance ($R_L$) in response to increasing doses of aerosol methacholine delivery. Error bar, SEM; n=5 per group. B. Real-time PCR analysis of inflammatory gene expression in lung tissue. *P<0.05 (HDF mice compared with HDF+A18 mice). C-D. WT C57BL/6 mice were sensitized intratracheally (i.t.) with HDM (*Dermatophagoides farina*, 100 μg per mouse) on day 0 and subsequently challenged (i.t.) with HDM (100 μg per mouse) from day 7 for 5 days. Lung resistance ($R_L$) measurement (C) and lung tissue collection for real-time PCR analysis of inflammatory genes (D) were performed after 72 h of last HDM challenge. HDM+A18 group of mice were i.p. injected with A18 (30 μg per mouse) daily for the whole experimental period. *P<0.05 (HDM mice compared with HDM+A18 mice).
Figure 5:
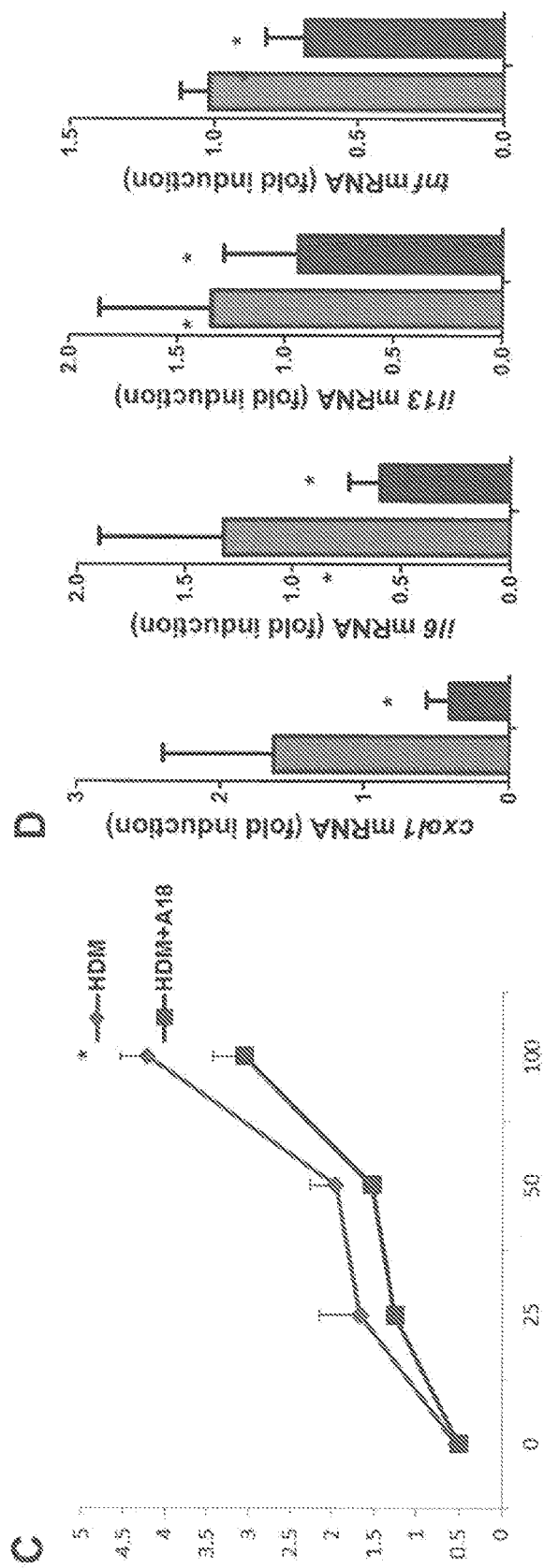

Recent studies suggest a role of IL-17A in the increased airway neutrophilia associated with severe asthma. Porsbjerg et al., Annals of allergy, asthma & immunology: official publication of the American College of Allergy, Asthma, & Immunology 98, 44-50, (2007). House dust mite (HDM) is a natural allergen to which asthmatics are often sensitized. Mice repeatedly challenged with HDM extract developed robust airway neutrophilia rapidly evolving into asthma-like disease with increased numbers of eosinophils and lymphocytes in bronchoalveolar lavages (BAL) as well as inflammatory infiltrates, vascular/muscular hypertrophy, interstitial fibrosis, epithelial hyperplasia and mucus accumulation in lung tissues. HDM-induced allergic asthma induces AHR and mixed TH2/TH17-driven inflammation, similar to the inflammatory phenotype observed in certain severe cases of asthma. Elevated levels of the cytokines IL-4, IL-5, IL-13, and IL-17 in bronchoalveolar lavage associated with an expansion of TH2 and TH17 cells in lung tissues were found in HDM-induced asthmatic mice. Both IL-17A deficiency and blocking anti-IL-17A antibody have been shown to alleviate HDM-induced AHR and airway inflammation, suggesting HDM-induced asthma model is an IL-17A-mediated disease model. Chesne et al., J Allergy Clin Immunol 135, 1643-1643 (2015). We thus evaluated whether A18 could modulate HDM-induced allergic airway disease. WT C57BL/6 female mice were sensitized intratracheally (i.t.) with HDM (*Dermatophagoides farina*, 100 µg per mouse) on day 0 and subsequently challenged (i.t.) with HDM (100 µg per mouse) from day 7 for 5 days. A18 were injected daily from day 0 through the whole experimental period. AHR measurement and tissue collection were performed after 72 h of last HDM challenge. As shown in FIG. 5C-D, HDM-induced AHR and inflammatory gene expression were both reduced by A18 treatment. Results from both HDM and HFD experiments imply the potential therapeutic role of A18 in treatment of IL-17A-mediated asthma.

A18 alleviated Th17-mediated experimental autoimmune encephalomyelitis (EAE). Secukinumab which neutralizes IL-17A, significantly lowered MS-type brain lesions and showed a trend toward reduced relapse rates in a 6-month, placebo-controlled trial in 73 patients. Currently Secukinumab is under extensive phase II clinical trials for treatment of MS patients. EAE is a well-established animal model for multiple sclerosis, a T cell-mediated inflammatory demyelinating disease of the human CNS. Recent studies have shown that IL-17A producing Th17 cells play a critical role in the development and pathogenesis of EAE. EAE is markedly suppressed in mice lacking IL-17A or IL-17 receptor (IL-17R), and IL-17A-specific inhibition attenuates inflammation, indicating that IL-17A-mediated signaling is important during the effector stage of EAE. Kang et al. Immunity 32, 414-425 (2010).

Therefore, Th17-mediated EAE is a suitable animal model to test IL-17A bioactivity in a disease setting. To test whether A18 can inhibit Th17-induced EAE, MOG 35-55-specific wild-type (WT) Th17 cells were adoptively transferred into C57Bl/6 WT recipient mice treated with or without A18. For A18-treated group, mice were continuously treated with A18 every other day after Th17 cell transfer. A18 administration substantially delayed onset of EAE and attenuated disease severity (FIG. 6A). A18-treated mice had greatly reduced expression of several IL-17-responsive inflammatory genes including CXCL1, IL6, GMCSF and Ccl20) and less infiltrated cells in spinal cords (FIGS. 6B and 6C). Interestingly, A18 did not affect infiltration of CD4+, CD8+ T cells and F4/80+ macrophages, whereas the recruitment of Ly6G+ neutrophils was substantially reduced in A18-treated mice (FIGS. 6D and 6E). This is consistent with well-known role of IL-17 as a potent inducer of neutrophil-chemoattractant chemokines such as Cxcl1. The above results indicate that A18 was indeed able to suppress Th17-mediated EAE, which may partly be due to attenuation of IL-17-dependent neutrophil recruitment to central nerve system.

A18 inhibited IL-17-induced skin hyperplasia and melanoma metastasis. We have recently identified a novel IL-17A signaling cascade via the specific interaction of IL-17R adaptor Act1 with TRAF4 to mediate MEKK3-dependent ERK5 activation that is critically important for keratinocyte proliferation and tumor formation. Notably, abnormal keratinocyte proliferation is also an important hallmark of pathogenesis of psoriasis, which is a well-defined IL-17A-dependent disease. Secukinumab (anti-IL-17A) showed extreme efficacy for psoriasis and was approved by FDA for treatment of psoriasis. Chiricozzi, A., Actas dermosifiliograficas 105 Suppl 1, 9-20 (2014).

To examine the impact of A18 on IL-17A-induced epidermal proliferation, the ears of C57Bl/6 mice were each injected intradermally with IL-17A (500 ng) with or without A18 (30 µg per mouse) for 6 consecutive days. Following the injections, the control mice (without A18) exhibited IL-17A-dependent epidermal hyperplasia, while the hyperplasia was greatly reduced in mice injected with A18 (FIG. 7A-B). RT-PCR analysis revealed higher levels of C-myc, Pled, and Steap4 in IL-17A-treated ears compared to the untreated, which was attenuated in A18-treated mice (FIG. 7C). Taken together, these data suggest that IL-17A induces keratinocytes proliferation, resulting in epidermal hyperplasia, which was effectively blocked by A18. Importantly, our recent results indicate that IL-17A-induced keratinocytes proliferation contributes to skin tumor formation, which implies the possible therapeutic value of A18 in cancer treatment.

Melanoma pulmonary metastasis is indicative of poor prognosis. The experimental lung metastasis has been used to test the ability of tumor cell migration, growth at distant sites, effects of drugs for treatment of lung metastasis. In this model, melanoma cells are injected through tail vein, and metastatic lesions can be established in the lung after 2-3 weeks. Here we used this experimental lung metastasis model to test the possible impact of A18 on melanoma re-establishment at distant lung tissue. D4M melanoma cells (Jenkins et al., Pigment cell & melanoma research 27, 495-501 (2014)), ($1 \times 10^6$ cells) were injected into C57BL/6 mouse through tail vein. The control group mice were injected with 200 µl PBS daily, the other group mice were injected with 60 µg A18/mouse daily. The Histological sections were obtained from lung tissue at day 20. Fewer and smaller lung metastasis tumors were observed in A18-treated mice compared to the PBS-treated control mice (FIG. 7D-F). These results suggest that A18 can suppress melanoma cell migration and growth, implicating the potential of A18 in treatment of melanoma metastasis.

Example II

Demonstration of Structure-Activity Relationship (SAR) of A18 for IL-17A Inhibition As a validated lead compound, A18 showed excellent IL-17A inhibition in biochemical binding assay, cell-based bioassay and in vivo animal studies. To further develop A18 to a drug candidate, it is important to define the critical elements and functional groups responsible for its inhibitory activities. This information will provide guidance for structural optimization of A18 by medical chemistry in future drug development.

Define the Importance of the Hydroxyl Groups Based on computational docking of A18 to IL-17RA binding pocket, all five —OH groups of A18 are involved in hydrogen bond formation with IL-17RA. Using existing compounds, we tested the importance of some of the hydroxyl groups for A18's inhibitory effect. We found that B3'-OH is critical for A18's inhibitory activity using IL-17A-IL-17RA binding assay since removal (pelargonidin) or modification (peonidin) of B3'-OH substantially increased IC50 (>100 µM) (FIG. 8A-B). We also tested whether removal (luteolinidin) or modification (cyanidin-3-O-glucoside) of C3-OH will affect the inhibitory activity (FIG. 8C). Interestingly, IC50s of both luteolinidin and cyanidin-3-O-glucoside in the in vitro inhibiting assay were still in a good range (198.4 nM and 96.4 nM respectively), suggesting that the C3-OH group might be less critical for the inhibitory activity. It should be noted another member of the anthocyanidins (A10, also called delphinidin, which has an additional —OH at B5' as compared with A18) has a comparable Glidescore and slightly improved IC50 with A18 (FIG. 8D).

To test the importance of —OH at A5, we synthesized A18Δ5OH (FIG. 8E). The removal of OH at A5 still retained some inhibitory activity in the in vitro inhibition assay (IC50>30 µM), but with much reduced potency compared to A18, demonstrating the importance of A5-OH for A18's activity (FIG. 8E).

Define the importance of the A-C-B ring structure Depending highly on temperature, pH and presence of light and oxygen, A18 (cyanidin) can spontaneously degrade to photocatechuic acid and phloroglucinol aldehyde. The fact that these natural products are susceptible to extensive metabolism presents important issues to address for improving their drug properties. We found that photocatechuic acid, the major A18 metabolite in vivo, exhibited greatly reduced inhibitory activity as indicated by both Glidescore and IC50 of inhibition (FIG. 8G), indicating that integrity of A-C-B ring structure of A18 is important to maintain its potent inhibitory activity.

To further test the importance of ring C, we synthesized A18C5 (FIG. 8F), in which the 6-membered ring C was replaced with 5-membered ring C. Importantly, A18C5 showed very little activity in in vitro inhibiting assay (IC50>100 μM)(FIG. 8F). These results indicate that the geometry of ring C in A18 is important for A18's activity.

A18 Analogs

Functional groups of ring A and B for better solubility, stability and potency: Based on our docking and initial structure-activity relationship (SAR) data, we found that B3'-OH ($R^4$) and A5-OH ($R^1$) are critical for A18's inhibitory activity using IL-17A-IL-17RA binding assay. We will replace the hydroxyl groups at $R^1$ and $R^4$ with amines, amides and cyanides, and with other hydrogen bond donor groups to improve potency of A18, and reduce metabolism of the hydroxyl groups. Furthermore, based on our docking, we learned that A7-OH ($R^2$) and B4'-OH ($R^5$) are in contact with the binding pocket. Thus, we will also modify $R^2$ and $R^5$ with amines, amides and cyanides to improve potency of A18. On the other hand, we learned that the C3-OH ($R^3$) and B5'-OH ($R^6$) are not important for A18's activity. Thus, we will replace this hydroxyl group with F, Cl or glycoside to improve stability; amine and ether for better solubility. Specific examples and their synthesis routes are shown in FIG. 10.

Figure 10D:
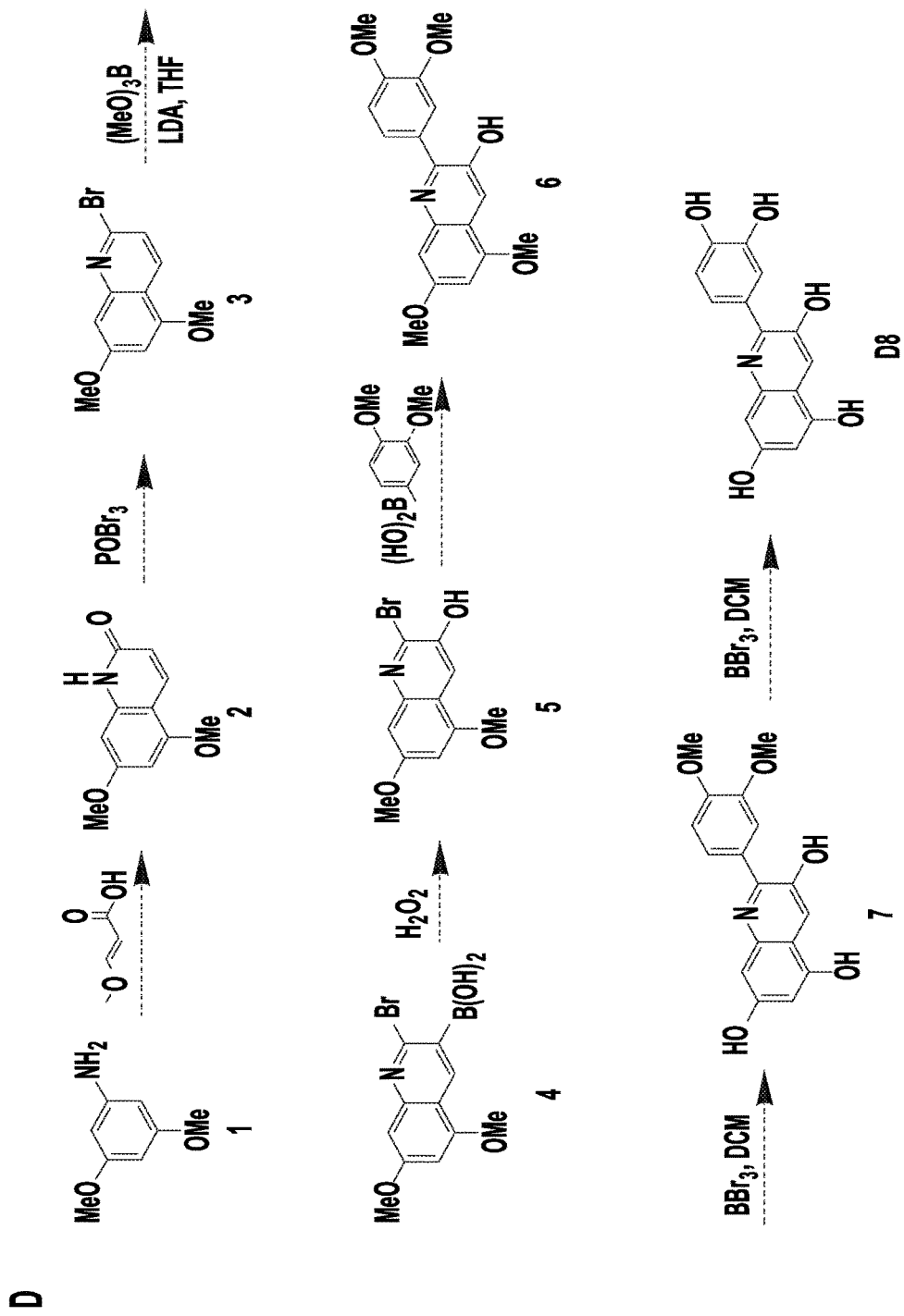

Modification of the ring structure to improve stability and potency: We found ring C is important for the function of A18. The positively charged oxygen ($O^+$) on the C ring of A18 is a unique structural feature considered for modification since it makes the $O^+$—C2 double bond susceptible to hydrolytic cleavage. Thus $O^+$ group in C ring will be replaced by C or N. A specific example and its synthetic route is shown in FIG. 10D. The C ring will also be reduced, replacing the $O^+$ group with an O. We will also replace ring A and/or B with a 6-membered heteroaryl ring such as pyridine to improve stability and potency, and to increase solubility.

Demonstration of Structure-activity relationship (SAR) of A0 for IL-17A inhibition. We found (−)catechin (A0), a flavan-3-ol subfamily member of flavonoid family, exhibited good Glidescore (−7.12) and IC50 (956 nM) in IL-17A-IL-17RA binding inhibition assay (FIG. 9). We also found other flavonoid members [including several other members of flavan-3-ols [e.g. gallocatechin, epigallocatechin, epicatechin gallate (EGC), epigallocatechin gallate (EGCG)], members of flavonols (e.g. quercetin), members of flavones (e.g. luteolin), and members of flavanonols (e.g. taxifolin)] all showed inhibitory activity for IL-17-IL-17RA binding with IC50 ranging from 300 nM to 10 μM.

A0 Analogs

The A0 series is based on a chromane scaffold, and lacks the positive charge ($O^+$) of some embodiments of the A18 series. Based on SAR generated in the A18 series, it is expected that hydroxyl groups at positions $R^1$, $R^4$, and $R^2$ make important contributions to binding potency due to interactions with IL-17RA. Hydroxyl substituents at $R^3$, $R^5$, $R^8$ and $R^6$ may contribute less to binding potency, and it may be possible to remove or replace these hydroxyl groups.

Phenolic groups are known to be metabolized by conversion to glucuronides, which may lose their binding affinity for IL-17RA, and may be rapidly excreted. Remove or replacement of the phenolic groups in the A0 series may reduce this potential liability. Molecules with two phenolic groups that are on carbon atoms ortho to each other (catechols) can be metabolized to ortho-quinones, which may be toxic due to addition of nucleophiles (e.g. cysteine side-chains). This potential liability may also be reduced or eliminated by removal or replacement of the phenolic groups.

In Formula II, one or more of the phenols present in the A0 series is replaced with another substituent as indicated. The secondary hydroxyl ($R^3$) may be independently replaced with one of the substituents indicated. In addition, the 0 group in C ring will be replaced by C or N.

Figure 11B:
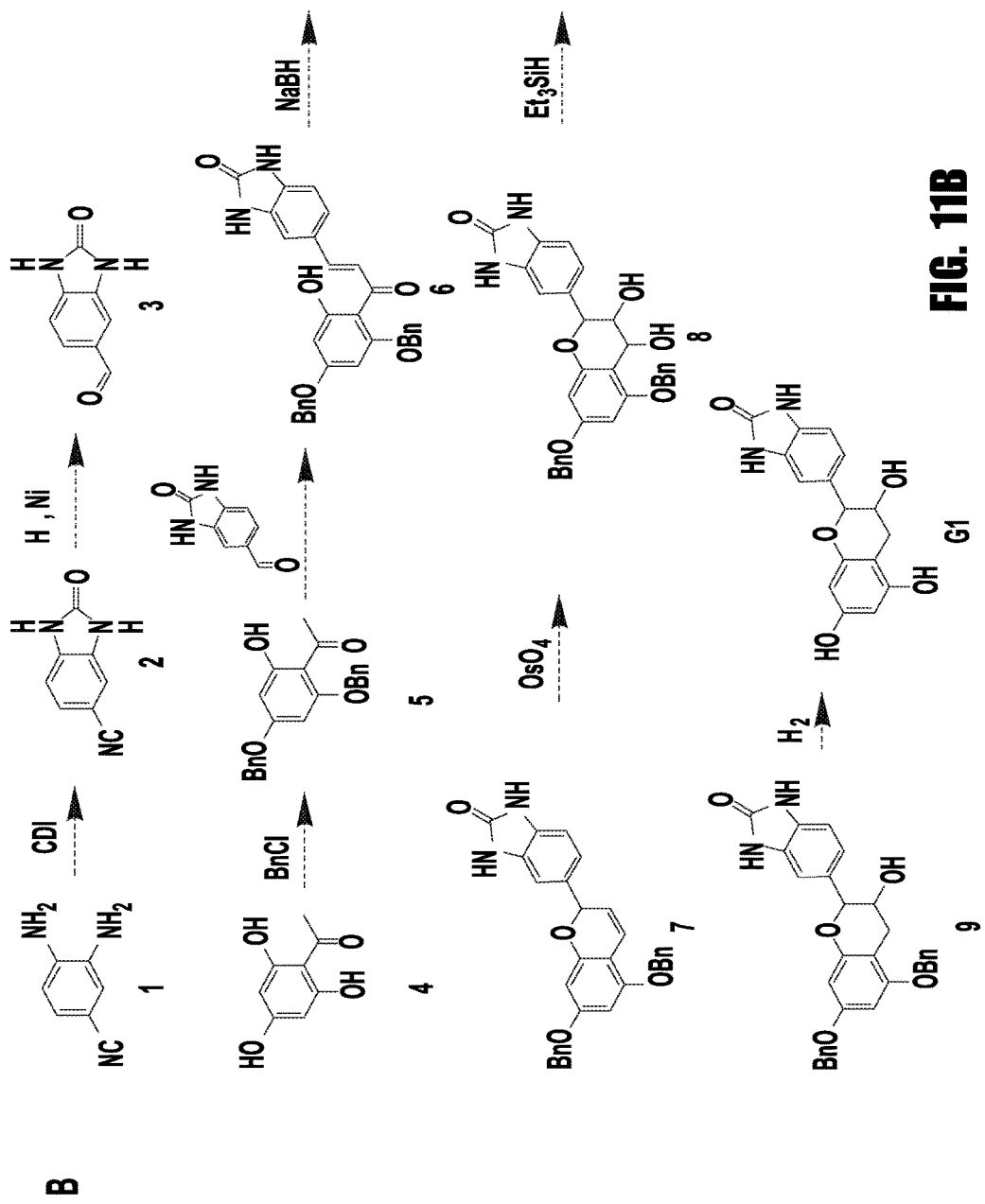

In Formula II, ring B of the A0 series (bearing substituents X', Y' and Z') is replaced by a bicyclic moiety Q, which incorporates a group capable of donating a hydrogen bond to IL-17RA. Phenolic groups X and Y on ring A may be independently replaced with substituents $R^4$ and $R^5$. The secondary hydroxyl (X") may be independently replaced with one of the substituents indicated. A specific example and its synthesis route are shown in FIG. 11B.

Figure 11C:
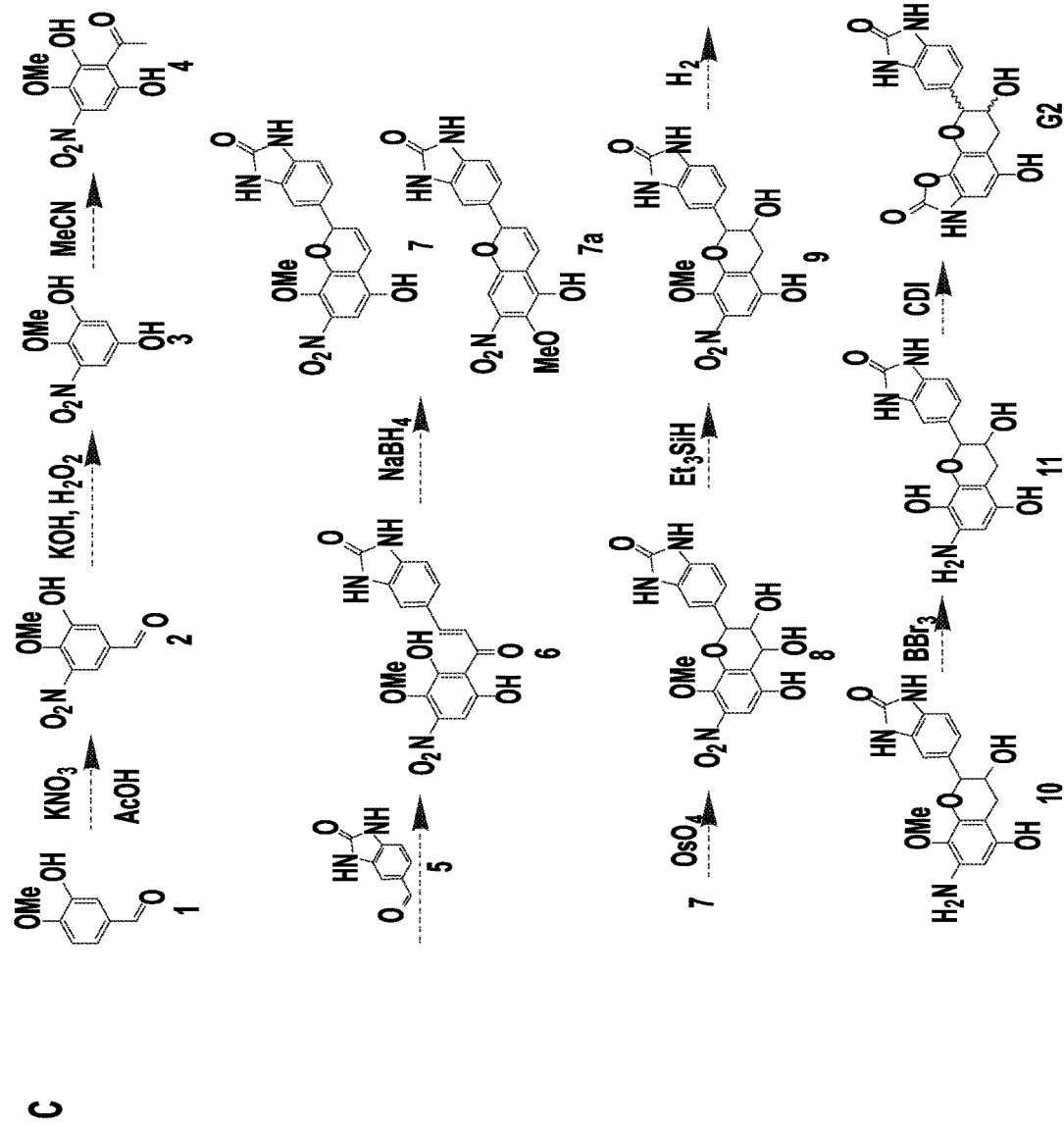
Figure 11D:
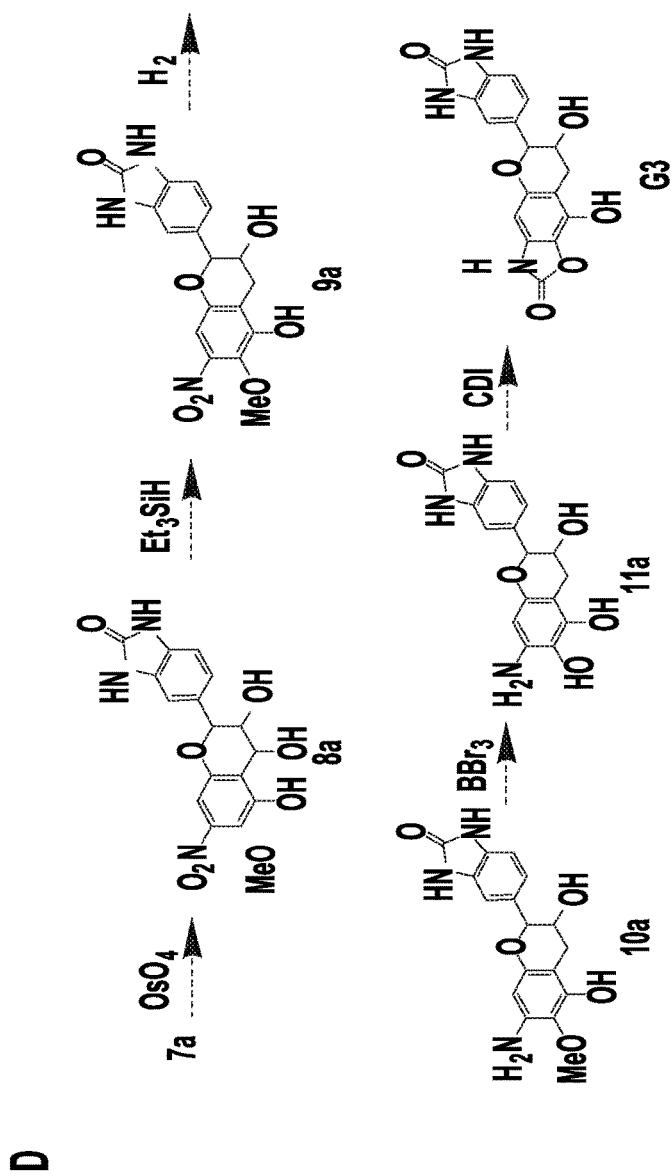
Figure 11E:
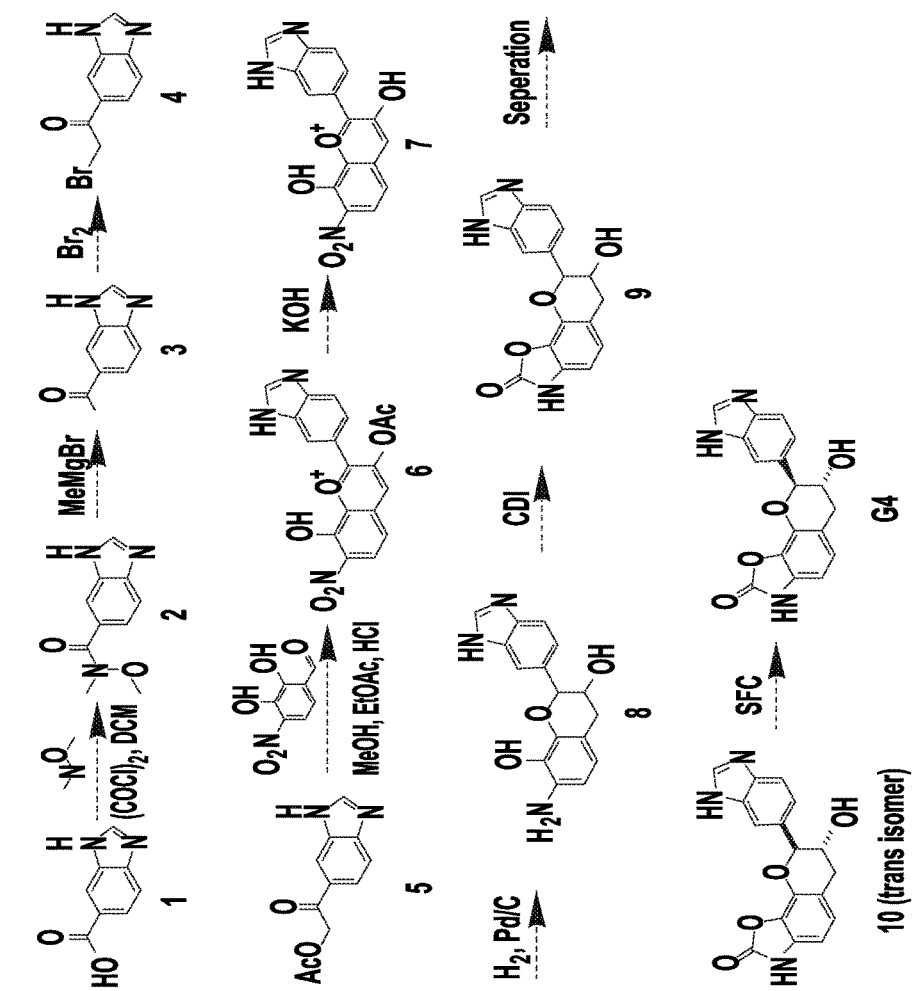

In Formula IV, ring B of the A0 series (bearing substituents $R^4$, $R^5$ and $R^6$) is replaced by a bicyclic moiety, which incorporates a group capable of donating a hydrogen bond to IL-17RA. Phenolic groups may independently be replaced with a ring E (shown as Ring A in formula IV) fused onto ring A. The new ring is capable of donating a hydrogen bond to IL-17A. The secondary hydroxyl ($R^3$) may be independently replaced with one of the substituents indicated. Specific examples and their synthesis routes are shown in FIGS. 11C and 11E.

In Formula V, ring B of the A0 series (bearing substituents $R^4$, $R^5$ and $R^6$) is replaced by a bicyclic moiety, which incorporates a group capable of donating a hydrogen bond to IL-17RA. Phenolic groups at $R^2$ and $R^8$ may be replaced with a ring E (shown as Ring A in formula V) fused onto ring A. The new ring is capable of donating a hydrogen bond to IL-17RA. The secondary hydroxyl ($R^3$) may be independently replaced with one of the substituents indicated. A specific example and its synthetic route is shown in FIG. 11D.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, while theories may be presented describing possible mechanisms through with the compounds are effective, the inventors are not bound by theories described herein. The invention is not limited to the exact details shown and described, for variations obvious to one skilled in the art will be included within the invention defined by the claims.

The invention claimed is:

1. A method of treating Th17 infiltrated/driven asthma in a subject, consisting of administering to the subject an effective amount of a pharmaceutical composition consisting of compound according to formula I:

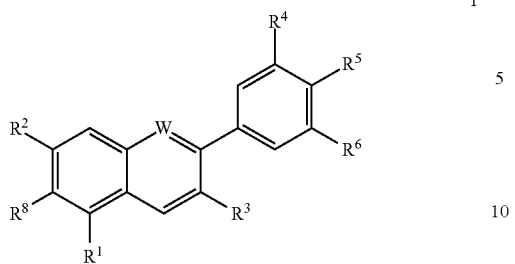

wherein $R^3$, $R^6$, and $R^8$ are independently selected from —H, —$C_1$-$C_4$ alkyl, —OH, —OMe, and halogen; $R^1$, $R^2$, $R^4$, and $R^5$ are —OH and wherein W is selected from the group consisting of —CH—, —$O^+$—, and —N—;

or a pharmaceutically acceptable salt thereof, and optionally a pharmaceutically acceptable carrier.

2. The method of claim 1, wherein W is—$O^+$—.

3. The method of claim 1, wherein the compound is cyanidin.

4. The method of claim 1, wherein the compound is delphinidin.

5. The method of claim 1, wherein the compound is administered by intravenous, intramuscular, or subcutaneous injection.

6. The method of claim 1, wherein the composition is administered by inhalation.

* * * * *

UNITED STATES PATENT AND TRADEMARK OFFICE
CERTIFICATE OF CORRECTION

PATENT NO. : 10,385,034 B2
APPLICATION NO. : 14/847307
DATED : August 20, 2019
INVENTOR(S) : Xiaoxia Li et al.

It is certified that error appears in the above-identified patent and that said Letters Patent is hereby corrected as shown below:

In the Specification

In Column 1, Line 15, please insert the following paragraph:
--This invention was made with government support under NS071998 and HL103453 awarded by the National Institutes of Health. The government has certain rights in the invention."--

Signed and Sealed this
Twentieth Day of September, 2022

Katherine Kelly Vidal
*Director of the United States Patent and Trademark Office*